(12) United States Patent
Pärkkä et al.

(10) Patent No.: US 12,678,059 B2
(45) Date of Patent: Jul. 14, 2026

(54) TECHNIQUES FOR DETERMINING BLOOD PRESSURE BASED ON A RELATIVE TIMING OF PULSES

(71) Applicant: Oura Health Oy, Oulu (FI)

(72) Inventors: Juha Pekka Pärkkä, Lempäälä (FI); Petri Määttä, Ylöjärvi (FI); Kimmo Pärssinen, Tampere (FI); Emmi Maria Johanna Antikainen, Pirkkala (FI); Miska Mikael Viljami Valkonen, Jyväskylä (FI)

(73) Assignee: Oura Health Oy, Oulu (FI)

( * ) Notice: Subject to any disclaimer, the term of this patent is extended or adjusted under 35 U.S.C. 154(b) by 0 days.

(21) Appl. No.: 18/499,587

(22) Filed: Nov. 1, 2023

(65) Prior Publication Data

US 2024/0315575 A1     Sep. 26, 2024

Related U.S. Application Data

(63) Continuation-in-part of application No. 18/189,888, filed on Mar. 24, 2023, now Pat. No. 12,433,497.

(51) Int. Cl.
| | |
|---|---|
| *A61B 5/021* | (2006.01) |
| *A61B 5/00* | (2006.01) |
| *A61B 5/024* | (2006.01) |

(52) U.S. Cl.
CPC ............ *A61B 5/021* (2013.01); *A61B 5/0077* (2013.01); *A61B 5/024* (2013.01); *A61B 5/6802* (2013.01);
(Continued)

(58) Field of Classification Search
None
See application file for complete search history.

(56) References Cited

U.S. PATENT DOCUMENTS

| | | | |
|---|---|---|---|
| 10,750,960 | B2 | 8/2020 | Miao et al. |
| 10,827,934 | B2 | 11/2020 | Oksala et al. |

(Continued)

FOREIGN PATENT DOCUMENTS

| | | |
|---|---|---|
| CN | 114680819 A | 7/2022 |
| EP | 3136954 A1 | 3/2017 |

(Continued)

OTHER PUBLICATIONS

International search Report and written opinion received for PCT application No. PCT/US2023/016430, mailed on Dec. 21, 2023, 14 pages.

(Continued)

*Primary Examiner* — Yi-Shan Yang
(74) *Attorney, Agent, or Firm* — ArentFox Schiff LLP

(57) ABSTRACT

Methods, systems, and devices for synchronizing multiple devices for determining physiological metrics are described. A method may include flashing light-emitting diodes (LEDs) of a wearable device, and capturing images of the flashing LEDs using an imaging device. A synchronization procedure may be performed to identify a delay between internal clocks at the wearable device and the imaging device based on capturing the images. Subsequently, the wearable device and the imaging device may collect physiological data at different physiological locations on the user's body, where the physiological data includes separate pulse observation times of a heartbeat of the user at the different physiological locations. Subsequently a pulse transmit time (PTT) associated with the heartbeat may be determined based on the delay and a comparison between the pulse observation times, and a blood pressure metric for the user is determined based on the PTT.

19 Claims, 12 Drawing Sheets

(52) U.S. Cl.
CPC .......... *A61B 5/6826* (2013.01); *A61B 5/7285*
(2013.01); *A61B 5/7435* (2013.01)

(56) References Cited

U.S. PATENT DOCUMENTS

| | | | |
|---|---|---|---|
| 11,925,441 B1 | 3/2024 | Rantanen et al. | |
| 2002/0058876 A1 | 5/2002 | Chen et al. | |
| 2003/0109791 A1 | 6/2003 | Kondo et al. | |
| 2010/0298726 A1 | 11/2010 | Kim et al. | |
| 2012/0029363 A1 | 2/2012 | Lund | |
| 2012/0179011 A1 | 7/2012 | Moon et al. | |
| 2017/0027459 A1 | 2/2017 | Shimuta | |
| 2017/0143216 A1 | 5/2017 | Oksala et al. | |
| 2017/0181649 A1 | 6/2017 | Carter et al. | |
| 2019/0060568 A1 | 2/2019 | Newberry et al. | |
| 2019/0110758 A1 | 4/2019 | Kang et al. | |
| 2019/0125198 A1 | 5/2019 | Kang et al. | |
| 2019/0286233 A1 | 9/2019 | Newberry | |
| 2020/0146630 A1 | 5/2020 | Joe et al. | |
| 2020/0237317 A1 | 7/2020 | Newberry et al. | |
| 2020/0297220 A1 | 9/2020 | Lu et al. | |
| 2020/0397311 A1 | 12/2020 | Jung et al. | |
| 2020/0405159 A1* | 12/2020 | Archdeacon | A61B 5/7278 |
| 2021/0022639 A1 | 1/2021 | Iwade et al. | |
| 2021/0030367 A1 | 2/2021 | Cho et al. | |
| 2021/0059585 A1 | 3/2021 | Choi et al. | |
| 2021/0153757 A1 | 5/2021 | Jeon et al. | |
| 2023/0055617 A1 | 2/2023 | Lange et al. | |
| 2023/0068620 A1 | 3/2023 | Tadele et al. | |
| 2024/0005432 A1* | 1/2024 | Aman | G16H 10/40 |
| 2024/0172945 A1 | 5/2024 | Park et al. | |
| 2024/0315574 A1 | 9/2024 | Rantanen et al. | |
| 2024/0315575 A1 | 9/2024 | Pärkkä et al. | |
| 2024/0315578 A1 | 9/2024 | Rantanen et al. | |

FOREIGN PATENT DOCUMENTS

| | | |
|---|---|---|
| WO | 98/17172 A2 | 4/1998 |
| WO | 2012/103296 A2 | 8/2012 |
| WO | 2014/089665 A1 | 6/2014 |
| WO | 2017/147609 A1 | 8/2017 |
| WO | 2017/212120 A1 | 12/2017 |
| WO | 2018/013569 A1 | 1/2018 |
| WO | 2020/105841 A1 | 5/2020 |
| WO | 2021/249850 A1 | 12/2021 |
| WO | 2022/115876 A1 | 6/2022 |
| WO | 2022/146881 A1 | 7/2022 |

OTHER PUBLICATIONS

Invitation to Pay Additional Fees received for PCT application No. PCT/US23/016430, mailed on Oct. 30, 2023, 11 pages.
Obata et al., "Noninvative assessment of the effect of position and exercise on pulse arrival to peripheral vascular beds in healthy volunteers", Frontiers in Physiology, 2017, vol. 8, Article 47 (Year: 2017).
International Search Report and Written Opinion received for PCT Patent Application No. PCT/US2023/016432, mailed on Nov. 3, 2023, 9 pages.
Liu et al, "A Preliminary Study on Multi-Wavelength PPG Based Pulse Transit Time Detection for Cuffless Blood Pressure Measurement", 38th Annual International Conference of the IEEE Engineering in Medicine and Biology Society (EMBC), 2016, pp. 615-618.
Notification of material filed by a third party received for Australian Patent Application No. 2023441282, mailed on Jan. 14, 2026, 17 pages.
Office Action received for European Patent Application No. 23718472. 6, mailed on Jan. 20, 2026, 5 pages.
Third Party Observation received for German Patent Application No. 112023003389.7, mailed on Jan. 16, 2026, 42 pages (18 pages of English Translation and 24 pages of Original Document).

* cited by examiner

User <u>102</u>

104-a

Location
<u>305-a</u>

Location
<u>305-b</u>

104-b

Pulse Observation Time Graph <u>310</u>

Heart
Rate
Pulses

Time

First Pulse
Observation Time
<u>310-a</u>
(First Location)

Second Pulse
Observation Time
<u>310-b</u>
(Second Location)

300

TECHNIQUES FOR DETERMINING BLOOD PRESSURE BASED ON A RELATIVE TIMING OF PULSES

CROSS REFERENCE

The present application for patent claims the benefit of U.S. patent application Ser. No. 18/189,849 by RANTA-NEN et al., entitled "TECHNIQUES FOR DETERMINING BLOOD PRESSURE BASED ON MORPHOLOGICAL FEATURES OF PULSES," filed Mar. 24, 2023, and U.S. patent application Ser. No. 18/189,888 by RANTANEN et al., entitled "TECHNIQUES FOR DETERMINING BLOOD PRESSURE BASED ON A RELATIVE TIMING OF PULSES," filed Mar. 24, 2023, which are both assigned to the assignee thereof, and expressly incorporated by reference herein.

FIELD OF TECHNOLOGY

The following relates to wearable devices and data processing, including techniques for determining blood pressure based on a relative timing of pulses.

BACKGROUND

The following relates to wearable devices and data processing, including techniques for determining blood pressure based on a relative timing of pulses.

DETAILED DESCRIPTION

Figure 1:
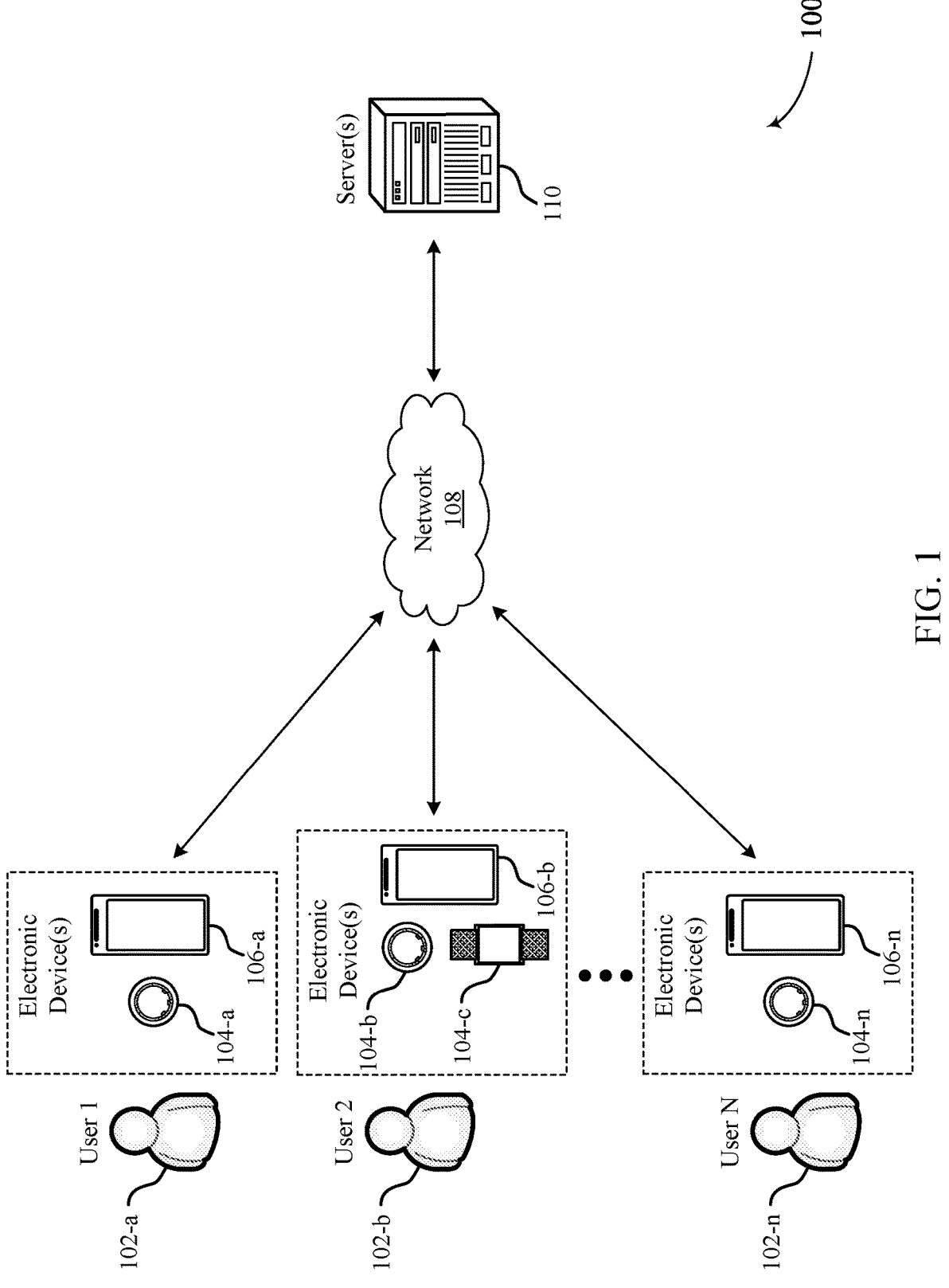
FIG. 1 illustrates an example of a system that supports techniques for determining blood pressure based on a relative timing of pulses in accordance with aspects of the present disclosure.

Traditionally, blood pressure has only been able to be measured in a clinical setting, resulting in users only having their blood pressure measured on the few occasions a year that they go into their doctor's office. At-home blood pressure devices have enabled users to measure their blood pressure at home. However, traditional blood pressure devices rely on bulky arm cuffs that are not comfortable (or feasible) to wear consistently.

Some wearable devices have attempted to use light-based measurements to perform blood pressure measurements. Wearable devices that have attempted to utilize light to acquire physiological data necessary for determining blood pressure may be unable to perform blood pressure measurements due to signal processing limitations. Other techniques may measure heartbeats at multiple points on the user's body, and may estimate blood pressure using "pulse transmit times (PTTs)," which is a measure of how long it takes for a heartbeat to travel from one part of the user's body to another. However, when using PTT to estimate blood pressure, timing offsets between devices may result in skewed PTT values, thereby resulting in inaccurate or unreliable blood pressure measurements.

Accordingly, aspects of the present disclosure are directed to systems that utilize one or more wearable devices (e.g., wearable ring devices, watches and bracelets, necklaces, chest-worn wearable devices, headbands or straps, extremity monitors) to determine one or more blood pressure metrics (e.g., measurements) of a user. Aspects of the present disclosure are directed to techniques for a blood pressure "spot check" where a wearable device (e.g., ring) and a camera (e.g., camera on a smartphone) are used to measure PTT of a user's heartbeat, where the PTT is then used to estimate blood pressure. More specifically, this application focuses on techniques for synchronizing internal clocks between the wearable device and the camera (or another wearable device) to improve timing synchronization between the respective devices, thereby leading to more accurate PTT and blood pressure estimation.

For example, upon initiating a blood pressure spot check, a user may hold their phone camera up to their ring as the ring strobes or flashes LEDs. By imaging the strobing LEDs with the phone camera, the system may be configured to observe delays between when LEDs are strobed at the ring, and when the strobing is observed by the camera. Such delays may be used to synchronize internal clocks at the phone and the ring, and/or adjust a timing of PPG segments measured by one of the devices during a "blood pressure spot check," as will be described in further detail herein. After determining the delay between the devices via the synchronization procedure, the user may hold the tip of their finger to the phone camera so that the system can determine PTTs for heart beats traveling from the base of the user's finger (where the heart beat is observed by the ring) to the tip of the user's finger (where the heart beat is observed by the phone camera). In this regard, the relative timing of PPG pulses observed by the ring (at the base of the finger) and the camera (at the fingertip) may be calibrated and used to determine PTT values by synchronizing the internal clocks at the devices, or shifting the PPG pulses observed by one of the devices during the blood pressure spot check by the delay determined during the synchronization procedure. In some cases, another synchronization procedure may be performed after performing the "blood pressure spot check." Subsequently, the observed PTT values may be used to estimate the user's blood pressure.

In additional or alternative implementations, synchronization techniques described herein may be used to synchronize internal clocks across devices by using sound-based measurements. For example, in some cases, a microphone of a user device (e.g., cell phone) may be held up to a user's chest to determine when the user's heart beats, and a wearable ring device may measure when the heartbeat reaches the user's finger, where the PTT may be used to determine physiological parameters, such as blood pressure, pulse wave velocity (PWV), arterial stiffness, arterial plaque, and the like. In such cases, a synchronization procedure may be performed in order to synchronize/coordinate measurements performed by the microphone of the user device and the wearable device. For example, during a synchronization procedure, a user may "knock," or tap, the wearable ring device against the user device. In this example, the system may be configured to use acceleration data from the wearable ring device and sound data from the microphone to identify the respective knocks/taps, and to identify delays between internal clocks of the respective devices. Such delays may be used to synchronize internal clocks at the user device (e.g., microphone) and the ring, and/or adjust a timing of PPG segments observed by the ring (or audio pulses observed by the microphone) during a "blood pressure spot check," as will be described in further detail herein.

Aspects of the disclosure are initially described in the context of systems supporting physiological data collection from users via wearable devices. Aspects of the disclosure are further illustrated by and described with reference to apparatus diagrams, system diagrams, and flowcharts that relate to techniques for determining blood pressure based on a relative timing of pulses.

FIG. 1 illustrates an example of a system 100 that supports techniques for determining blood pressure based on a relative timing of pulses in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time that the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for determining blood pressure based on a relative timing of pulses. That is, system 100 may use one or more wearable devices 104 (e.g., chest-worn wearable devices, wearable ring devices, wearable watches) to determine blood pressure metrics of a user 102. That is, the system 100 may enable the wearable devices 104, that are worn by users 102 on a daily basis, to determine blood pressure based on a relative timing of pulses (e.g., heartbeat pulses) of the user 102. Additionally, or alternatively, aspects of the present disclosure may use one or more wearable devices and one or more additional devices (e.g., camera or microphone of a user device) to identify heartbeats at different physiological locations, where the relative timing of the heartbeats may be used to determine a PTT and/or other physiological metrics, such as PWV, arterial stiffness, blood pressure, arterial plaque, and the like. As such, aspects of the present disclosure may enable more frequent blood pressure measurements, which may provide users with a more comprehensive picture of their overall health.

Varying blood pressures may cause heartbeat pulses to propagate to different parts of the body at varying speeds. For example, a higher blood pressure may cause heartbeats to propagate throughout the body at a faster rate, while a lower blood pressure may cause heartbeats to propagate throughout the body at a faster rate. As such, the system 100 may use the one or more wearable devices 104 placed at relative locations on the user 102, to acquire physiological data from the one or more wearable devices 104, to determine a pulse time associated with the heartbeat pulses, and to determine a blood pressure metric for the user 102 based on the pulse time.

In some implementations, the system 100 may use multiple wearable devices 104 placed at different locations of the body (e.g., chest, finger, wrist, ankles, or the like) to determine blood pressure metrics for the user 102. For example, a first wearable device 104-a at a first physiological location of the user 102 (e.g., chest) and a second wearable device 104-b at a second physiological location of the user 102 (e.g., wrist, finger, ankle) may acquire respective physiological data from the user 102. The physiological data may indicate a first pulse observation time of a heartbeat of the user 102 at the first physiological location, a second pulse observation time of the heartbeat, an additional heartbeat of the user 102, or both. Further, the system 100 may compare the first pulse observation time to the second pulse observation time to determine a pulse time (e.g., a time difference of pulses) associated with the heartbeat. As such, the system 100 may determine a blood pressure metric for the user 102 based on a comparison of the pulse times.

Additionally, or alternatively, the system 100 may use a combination of wearable devices and other devices (e.g., camera or microphone of a user device 106) placed at different locations of the body (e.g., chest, finger, wrist, ankles, or the like) to determine physiological metrics for the user 102. For example, a wearable ring device 104 may measure when heartbeats arrive at the base of the user's finger, and a camera of a user device may take images of the user's fingertip to determine when such heartbeats arrive at the tip of the finger, where the PTT of the heartbeats between the base and tip of the finger may be used to determine physiological metrics (e.g., blood pressure, arterial stiffness, PWV, etc.). By way of another example, a user may hold the user device 106 up to their chest so that a microphone of the user device 106 can collect sound information (e.g., sound pulses) that are used to identify when the user's heart beats. Similarly, a wearable ring device 104 may collect PPG data to determine when the heartbeats arrive at the user's finger in order to determine PTTs and other physiological metrics.

Additionally, or alternatively, the system 100 may use a single wearable device (e.g., a first wearable device 104-a) to determine the blood pressure metric for the user 102 based on when pulses arrive at different layers of tissue. For example, the wearable device 104-a may include one or more light emitting components (e.g., one or more LEDs) and photodetectors to receive light from the one or more light emitting components. The light emitting components and photodetectors may be coupled to a controller to transmit light associated with one or more wavelengths. Further, the wearable device 104-a may use the received light at the photodetector to acquire first physiological data from the user 102. In some examples, the first physiological data may indicate a first pulse observation time of a heartbeat of the user 102 at a first tissue penetration depth (e.g., at the epidermis, at the hypodermis). The wearable device 104-a may acquire a second physiological data from the user 102, where the second physiological data may indicate a second pulse observation time of the heartbeat, an additional heartbeat of the user, or both at a second tissue penetration depth (e.g., at the dermis). In some examples, the wearable device 104-a may determine that heartbeat pulses arrive at one or more capillaries located at the first layer (e.g., at a tissue layer closest to the skin of the user 102) faster than heartbeat pulses at one or more arteries located at the second layer (e.g., at a deeper tissue layer farther from the skin of the user 102). As such, the system 100 may determine a pulse time associated with the heartbeat, the additional heartbeat, or both, based on a comparison between the first pulse observation time and the second pulse observation time. In addition, the system 100 may use the pulse time to determine the blood pressure metric for the user 102. Thus, the system 100 may use the time it takes for pulses to reach different layers of tissues for determining the blood pressure of the user 102.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
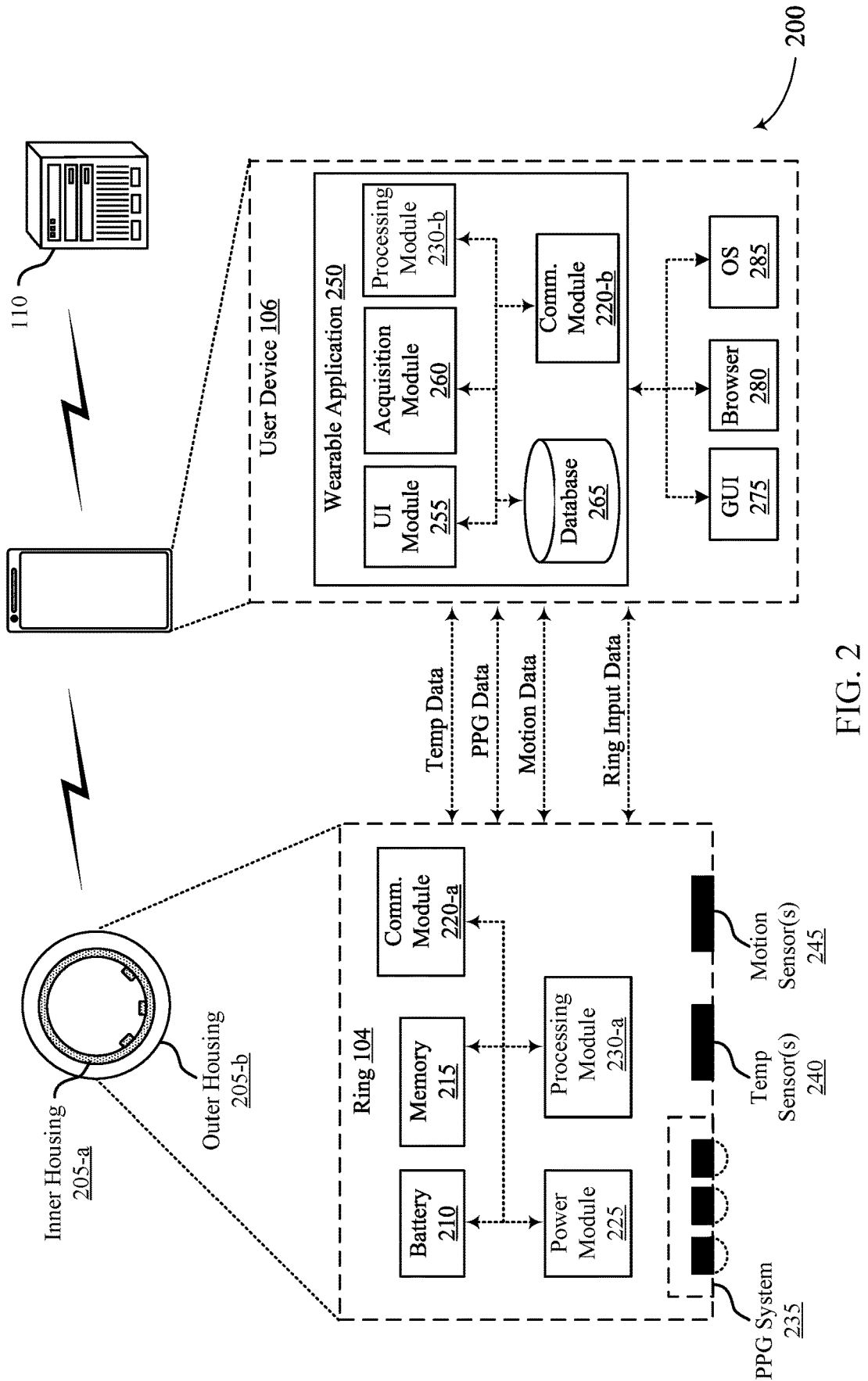
FIG. 2 illustrates an example of a system that supports techniques for determining blood pressure based on a relative timing of pulses in accordance with aspects of the present disclosure.

FIG. 2 illustrates an example of a system 200 that supports techniques for determining blood pressure based on a relative timing of pulses in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/ different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/ external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals.

For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least $0.5°$ C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for determining blood pressure based on a relative timing of pulses (e.g., heartbeat pulses). To provide some context for the desire to determine blood pressure, in some examples, one or more users (e.g., individuals) 102 may measure blood pressure regularly in a clinical setting, and therefore users 102 may measure blood pressure infrequently (e.g., once a year, twice a year). In addition, users 102 may not only fail to measure blood pressure but also health measurements related to heart rate, heart rate variability, cardiovascular age, arterial stiffness, AFib, ectopic beats, orthostatic tests, $VO_2$ max, and the like. As such, users 102 may unknowingly fail to take preventative actions based on whether the health measurements indicate positive or negative measurements.

That is, if users 102 were aware of one or more health measurements, the users 102 may integrate healthy life choices that include improving nutrition (e.g., eating fruits and vegetables), physical activity, sleep, stress management, or the like. However, as discussed, users 102 rarely attend primary care facilities, where one or more doctors may measure the cardiovascular health of users (e.g., run an electrocardiogram (ECG) test, measure consecutive heartbeat pulses), and therefore users 102 may be unaware of the risk factors, such as an increased risk of heart attack, stroke, heart failure, and other complications.

In particular, users 102 affected by cardiovascular health issues may implement lifestyle choices (e.g., changes) to improve overall cardiovascular health for the long term. For example, users 102 monitoring cardiovascular health may be concerned about risk factors of heart disease and/or stroke and may refrain from an unhealthy diet (e.g., a high salt intake), a lack of physical inactivity, tobacco use, alcohol, or the like. The user 102 may refrain from these actions to avoid an increase in blood pressure, an increase in blood glucose, or an increase in blood lipids that may lead to the user 102 becoming overweight and/or obese. In some examples, users 102 may be concerned about one or more cardiovascular health measurements, such as cardiovascular age, otherwise known as heart age and vascular age. Specifically, heart age is an assessment of well-known risk factors for heart disease (e.g., age, sex, blood pressure, cholesterol) to estimate a user's 102 risk of a heart attack or stroke compared to a defined healthy range. In some cases, when the heart age exceeds the current age of a user 102, the user 102 may be at modifiable risk for developing heart disease.

In other examples, users 102 may be concerned about vascular age, where a vascular age test provides a measurement of the apparent age of users' 102 arteries, compared to healthy users 102. In some instances, the user 102 may display a vascular age that exceeds the user's 102 chronological age and that the user 102 may be at risk for developing a cardiovascular disease (CVD). As such, affected users 102 may implement lifestyle changes such as increasing aerobic exercise, reducing calories, reducing sodium, including flavonoids in the diet, and other healthy dietary patterns to reduce arterial stiffness and blood pressure to reduce vascular aging. In some aspects, the tests that produce cardiovascular age measurements may compare one user's 102 data against multiple users 102. That is, the tests may compare the user's 102 pulse waveform to typical pulse waveforms across different age groups.

In some aspects, cardiovascular health measurements may utilize blood pressure measurements to accurately predict the user's 102 health and wellbeing. That is, blood pressure may indicate binary information that includes a systolic blood pressure measured from one or more arteries when the user's 102 heart beats and diastolic blood pressure measured from one or more arteries when the user's 102 is in between heart beats. In some examples, a classification of blood pressure may include either a normal blood pressure or a high blood pressure. For users 102, a normal blood pressure may indicate a systolic blood pressure of less than 130 millimeters of mercury (mmHg) and a diastolic blood pressure of less than 80 mmHg. Alternatively, a high blood pressure may indicate a systolic blood pressure greater than 130 mmHg and a diastolic blood pressure greater than 80 mmHg.

In some aspects, blood pressure measurements may indicate the pressure of circulating blood against the walls of blood vessels. In some cases, the blood pressure may result from the heart of the user 102 pumping blood through the circulatory system. That is, the heart pumps blood in the form of pulses (e.g., beats), where each pulse has a morphology (e.g., morphological features that describe the size/shape of pulses). Further, each pulse may indicate a different morphology (e.g., size and shape) that corresponds to blood pressure (e.g., high or low). For example, pulses acquired in different methods, such as PPG pulses and arterial blood pressure (ABP) pulses, may indicate different systolic peaks, diastolic peaks, dicrotic notches, pulse widths, slopes of pulses, inflection points, and the like.

In some examples, a comparison of pulses may illustrate differences as a result of PPG pulses acquiring signals non-invasively (e.g., a finger clip device) and ABP pulses acquiring signals invasively (e.g., inserted via a needle directly to a vein of the user). Further, the PPG pulses and ABP pulses may be compared on a graph over time to determine an in-phase analysis. That is, a morphology correlation (e.g., r) may be determined between the PPG and ABP waveforms to accurately determine whether the user falls under a specific blood pressure category, such as normotensive (e.g., normal blood pressure), prehypertensive (e.g., at risk for high blood pressure), or hypertensive (e.g., high blood pressure). As such, for a system to measure blood pressure accordingly, the system may utilize multiple pulses to properly indicate corresponding blood pressure categories of users 102 and determine whether users 102 are at risk for specific blood pressure conditions or diseases.

In some examples, the pulses may be monitored via a spot check, where a binary classification may indicate if the pulse exhibits a normal value or a high value. In other cases, the pulses may be evaluated against a blood pressure trend (e.g., a blood pressure trendline). That is, the pulses may be compared to typical blood pressure trends for the user expressed at different times of the day. In some cases, the pulses may be acquired over a term period (e.g., weekly, monthly, yearly). As such, blood pressure over some amount of time may compare blood pressure of the user that may include the sum of nocturnal, continuous blood pressure. In such instances, constant monitoring (e.g., chronic exposure) of blood pressure may be a key indicator (e.g., determinant) of cardiovascular risk. That is, the area under the curve of blood pressure, in other words the cumulative cardiovascular risk, may be calculated by time multiplied by continuous blood pressure (e.g., area under the curve=time*continuous blood pressure). In some examples, pulses may be compared to typical blood pressure trends at night to determine if a user has nocturnal hypertension based on a dipping of pulses. For the user, a normal, nocturnal blood pressure trend may indicate a blood pressure dipping about 10% to 15% less than typical daytime pulses. However, detecting blood pressure changes (e.g., blood pressure changes based on absolute values and additional values) greater than 15% may indicate a warning that the user has an elevated sodium level, a salt sensitivity, chronic kidney disease (CKD), congestive heart failure (CHF), diabetes, a structural vascular disease, insomnia, or the like. In addition, the U.S. Food and Drug Administration (FDA) permits monitoring pulses via spot checks or blood pressure trends to detect blood pressure of users, and therefore techniques that support these methods would be beneficial to integrate to users outside of a hospital setting.

In some aspects, one or more health care workers (e.g., nurses, doctors) may use a blood pressure device (e.g., a sphygmomanometer, a blood pressure cuff, a blood pressure monitor) that overlooks one or more pulses and determines blood pressure metrics for each user 102. In some examples, the user 102 may use an at home blood pressure device to acquire blood pressure metrics outside a clinical setting. However, the blood pressure device may use one or more arm cuffs that may be uncomfortable for the user to wear consistently. That is, one or more solutions that conveniently measure blood pressure on an everyday basis may enable the user 102 to monitor health issues. However, conventional wearable devices 104 have been unable to perform blood pressure measurements due to signal processing limitations and a lack of information about the relationship between blood pressure and features of PPG waveforms. Thus, methods and/or techniques for conveniently measuring blood pressure on a consistent basis may be desired but yet to be implemented.

Accordingly, the system 200 of the present disclosure may support techniques for determining blood pressure based on a relative timing of pulses. That is, the system 200 may use one or more wearable devices 104 (e.g., one or more wearable ring devices, watches, chest-worn monitors) and/ or additional devices (e.g., camera or microphone of a user device 106) to determine the blood pressure of a user 102. As such, the system 200 may use the one or more wearable devices 104 placed at relative locations on the user 102, to acquire physiological data from the one or more wearable devices 104, to determine a pulse time associated with the one or more heartbeats, and to determine a blood pressure metric for the user 102 based on the pulse time.

In this example, FIG. 2 shows a single wearable device 104 connected to a user device 106, however the system 200 may include additional wearable devices 104 (not illustrated) configured to communicate with the user device 106. That is, in some cases, the system 200 may use multiple wearable devices 104 (e.g., chest-worn wearable devices, wearable ring devices, wearable watches) placed at different physiological locations (e.g., parts) of the body (e.g., chest, finger, wrist, ankles, or the like) to determine the blood pressure metric for the user 102.

For example, a first wearable device 104 at a first physiological location of the user 102 and a second wearable device 104 at a second physiological location of the user 102 may acquire respective physiological data from the user 102. That is, one or more heartbeats propagate from the user's 102 heart to different locations of the body (e.g., fingers, toes, the head, and the like) of the user 102. In this example, the one or more heartbeats may be used interchangeably with one or more pulses. In some cases, a pulse may propagate to different physiological locations at varying speeds based on the variable blood pressure of the user 102. For example, a higher blood pressure may be indicative of pulses traveling faster to different physiological locations, while a lower blood pressure may be indicative of pulses traveling slower to different physiological locations. That is, fluctuating blood pressures with according speeds may result in pulses reaching different physiological locations at different times.

In some examples, the system 200 may acquire physiological data that indicates pulse observation times of the one or more heartbeats. In some aspects, the system 200 may acquire first physiological data from the user 102 via the first wearable device 104 that indicates a first pulse observation time of a heartbeat of the user at the first physiological location and second physiological data from the user 102 via the second wearable device 104 that indicates a second pulse observation time of the heartbeat, an additional heartbeat of the user, or both. In some cases, the wearable devices 104 may use the PPG system 235 that includes one or more light emitting components (e.g., LEDs) and photodetectors near the surface of the skin to measure the volumetric variations of blood flow of the user 102. In some examples, a triple LED (e.g., red, green, and IR) PPG system 235 may enable the wearable devices 104 to propagate multiple light waves into the tissue of the user 102 based on the wavelength of light to acquire physiological data. That is, the PPG system 235 may enable the system 200 to acquire the first physiological data that may include first PPG data via the first wearable device 104 at the first physiological location and second physiological data that may include second PPG data via the second wearable device 104 at the second physiological location.

Additionally, or alternatively, the first physiological data may include acceleration data (e.g., movement/motion data), ECG data, or both. In some cases, the wearable devices 104 may acquire acceleration data from the one or more motion sensors 245. That is, the system 200 may use the ECG and acceleration data to identify the one or more pulses at the chest of the user 102 in combination with the PPG data from the second physiological data to determine when the one or more pulses arrive at an extremity of the user 102.

Further, the first physiological data may indicate the first pulse observation time and the second physiological data may indicate the second pulse observation time. The respective pulse observation times may indicate the time that pulses were observed at the respective distal places on the body (e.g., a finger, an earlobe, a toe, or the like). As such, pulse observation times may be used to determine pulse times (e.g., PTTs) that indicate how long it takes for pulses to travel from one part of the body to another.

For the system 200 to determine the one or more pulse observation times of one or more heartbeats, one or more healthcare workers may conduct an ECG test, where an electrical signal from the heart of the user 102 is checked for heart conditions and one or more pulse observation times may be monitored. For example, the ECG test may monitor one or more pulse observation times, such as pulse transit times (PTTs) and pulse arrival times (PATs) that indicate the time that elapses for a pulse to reach different locations of a body of one or more users 102. That is, a PTT may indicate a time period for a pulse to travel from one arterial site to another arterial site (e.g., a time difference between pulse arrival times for two peripheral site PPGs). In other examples, a PAT may indicate a time interval for a pulse wave to travel from the heart of the user 102 to one or more distal places on the body. That is, the PAT may consider the PTT in addition to the pre-ejection period (PEP), where the PEP is a time period where no blood is ejected in addition to the time necessary to convert the electrical signal into a mechanical pumping force and the isovolumetric contraction of the left ventricle to open the aortic valve in the heart of the user 102. In some examples, pulse observation times may be compared to estimate an accurate blood pressure of the user 102. For example, the system 200 may compare a PTT that represents a first pulse observation time and a PAT that represents a second observation time to estimate blood pressure for the user 102. As such, the system 200 may observe multiple pulse observation times to determine when one or more pulses arrive at different parts of the body of the user 102 (e.g., ECG at the heart to the PPG pulse at the finger, or PPG at the wrist then the finger).

Upon determining pulse observation times, the system 200 may determine a pulse time (e.g., PTT, a time difference of pulses) associated with the one or more heartbeats. That is, the system 200 may compare the respective pulse observation times, such as a comparison between the first pulse observation time when one pulse reaches the first physiological location and the second observation time when the one pulse reaches the second physiological location, to determine a blood pressure metric for the user 102. Additionally, or alternatively, the system 200 may compare the first pulse observation time when the one pulse reaches the first physiological location and the second pulse observation time when an additional pulse reaches the second physiological occasion to determine a blood pressure metric for the user 102. That is, the system 200 may utilize multiple wearable devices 104 that are worn at different physiological locations and may compare different pulse observation times to determine according blood pressure metrics of the user 102.

Additionally, or alternatively, the system 200 may use a single wearable device 104 to determine the blood pressure metric for the user 102 based on when pulses arrive at different layers of tissue. For example, the wearable device 104-*a* may use the triple LED (e.g., red, green, and IR) PPG system 235 to enable the wearable device 104 to propagate multiple light waves into the tissue of the user 102 based on the wavelength of light. That is, the penetration depth (e.g., wavelength range) of light into the skin of the user 102 increases with wavelength from the UV to the visible light range and through the IR range. In some cases, the penetration depth of light into the skin of the user 102 may vary as a LED to penetration depth distance may be fixed to a specific range, however a signal may reach a further penetration depth as different wavelengths of light may be used. In the system 200, the light emitting components and photodetectors may be coupled to a controller to transmit light associated with one or more wavelengths. For example, the controller of the wearable device 104 may transmit a blue light associated with a wavelength of approximately 460 nanometers (nm), a green light associated with a wavelength of approximately 530 nm, a red light associated with a wavelength of approximately 660 nm, and/or an IR light associated with a wavelength of approximately 940 nm, where each of the transmitted wavelengths of light may reach one or more layers of tissue (e.g., an epidermis layer at around 0.3 millimeters (mm), a dermis layer at around 1.0 mm, a hypodermis layer at around 3.0 mm). That is, each of the transmitted lights may reach the one or more layers of tissues where the blood vessels are located, such as the capillaries located closest to the skin of the user 102 at the epidermis, the arterioles located at the middle layer at the dermis, and the arteries located at the deepest layer at the hypodermis. As such, the system 200 may use the light emitting component and the photodetector coupled to a controller on the wearable device 104 to transmit one or more lights associated with wavelength ranges to one or more tissue layers at multiple locations to acquire physiological data.

In some implementations, the system 200 may acquire physiological data via one or more pressure sensors 246. In some examples, first physiological data may be acquired during a first time interval associated with a first pressure applied between the wearable device 104 and a tissue layer. Additionally, a second physiological data may be acquired during a second time interval associated with a second pressure applied between the wearable device 104 and a tissue layer. In some aspects, the system 200 includes the wearable device 104 with an optical sensor that contacts the skin of the user 102 and the optical sensor may restrict blood circulation at different skin tissue layers. As such, varying pressures applied to the wearable device 104 may cause a respective wavelength of light to penetrate to different tissue penetration depths, and therefore identify heartbeat pulses at different penetration depths. In some cases, pressure between the optical sensor and the skin of the user 102 may incrementally increase the pressure and subsequently each of the tissue layers may be blocked and the PPG system 235 may be unable to transmit light from the one or more light emitting components through tissue layers. In some examples, external pressure may be applied to the optical sensor when the user 102 grabs an object, when the user 102 has swollen extremities (e.g., fingers) due to dehydration, or the like.

In some cases, the user 102 may apply the first pressure during the first time interval and/or the second pressure during the second time interval to acquire the first physiological data, the second physiological data, or both. In That is, the PPG system 235 may detect changes in one or more pulses (e.g., PPG pulses) from the light emitting components (e.g., different colors of light) due to the external pressure detected by the pressure sensor 246 that indicates pressure from the optical sensor acting against a vein internal pressure (e.g., blood pressure) of the user 102. That is, the system 200 may determine a correlation between arterial blood pressure and one or more pulse morphology (e.g., shape) obtained from the capillaries located closest to the skin of the user 102 at the epidermis, the arterioles located at the middle layer at the dermis, and the arteries located at the deepest layer at the hypodermis.

In some examples, the first physiological data may include PPG data and the second physiological data may include pressure data (e.g., bioimpedance data, piezoelectric data, or both). As such, the system 200 may determine a correlation between arterial blood pressure and pulse morphology and may account for external pressure when determining blood pressure of the user 102. Moreover, in some aspects, pressure sensors (e.g., piezoelectric sensors) may be used identify vibrations or other pressure changes attributable to heartbeats, which may be used to determine when heartbeats are detected (e.g., pulse arrival times), and may therefore be used to determine blood pressure metrics for the user.

In some aspects, the system may be configured to identify other circumstances or characteristics of the wearable device 104 and/or the user 102 that affect signal qualities or characteristics, such as user skin temperature, ring rotation/fit (e.g., tightness or looseness of the ring, as determined using pressure sensors or PPG sensors). In such cases, the system may be configured to identify how such characteristics affect blood pressure metrics, and compensate for such characteristics when determining blood pressure metrics of the user. That is, PPG signals may be compensated using data from other sources, such as pressure sensors, temperature sensors, and the like.

Additionally, or alternatively, the first physiological data and/or the second physiological data may include acceleration data (e.g., movement/motion data) associated with the user 102. In some cases, the wearable devices 104 may acquire acceleration data from the one or more motion sensors 245. For example, the wearable device 104 may use the motion sensors 245 to determine the heart rate of the user 102 when the user 102 is in motion (e.g., exercising). That is, the system 200 may use acceleration data to indicate how motion affects blood flow and subsequently blood pressure.

Further, the single wearable device 104 may use the PPG system 235 to acquire the first physiological data from the user 102. In some examples, the first physiological data may indicate a first pulse observation time of a heartbeat of the user 102 at a first tissue penetration depth (e.g., at the epidermis, at the dermis). In addition, the wearable device 104 may acquire the second physiological data from the user 102, where the second physiological data may indicate a second pulse observation time of the heartbeat, an additional heartbeat of the user, or both at a second tissue penetration depth (e.g., at the dermis, at the hypodermis). That is, the system 200 may transfer the PPG data from the wearable device 104 to the one or more user devices 106 to process the data. In some examples, the system 200 may determine that heartbeat pulses arrive faster at one or more capillaries located at the first layer (e.g., at a tissue layer closest to the skin of the user 102) and heartbeat pulses arrive later at one or more arteries located at the second layer (e.g., at a deeper tissue layer farther from the skin of the user 102). As such, the system 200 may enable the controller to determine a pulse time associated with the heartbeat, the additional heartbeat, or both, based on a comparison between the first pulse observation time and the second pulse observation time. Further, the system 200 may use the pulse time to determine a blood pressure metric for the user 102. Thus, the system 200 may use a single wearable device 104 to measure the time that elapses for pulses to reach different tissue penetration depths to determine the blood pressure of the user 102. As described herein, the system 200 may determine blood pressure metrics of the user 102 and may utilize acceleration data from the one or more motion sensors 245 to selectively adjust the blood pressure metrics of the user 102.

In some aspects, the system 200 may transfer physiological data with pulse observation times of one or more pulses for physiological locations and/or penetration depths from the one or more wearable devices 104 to the one or more user devices 106. That is, the user device 106 may determine the blood pressure metrics of the user 102 upon acquiring the physiological data. In some aspects, the user device 106 may store blood pressure trends for the user 102 in the database 265. That is, the blood pressure trends may indicate normal (e.g., typical) blood pressure levels of the user 102 and may indicate a baseline blood pressure metric associated with the user 102. Further, the user device 106 may compare the current blood pressure metric to the baseline blood pressure metric for differences (e.g., deviations). In some cases, the user 102 may determine notable differences between the baseline blood pressure metric of the user 102 and the current blood pressure metric of the user 102 and may use a GUI 275 of the user device 106 to display information associated with the differences. As such, the GUI 275 may alert (e.g., notify) the user about current blood pressure metrics of the user 102 in comparison to typical blood pressure trends of the user 102 and/or additional instructions for the user 102 to follow in order to calibrate blood pressure metrics.

Figure 3:
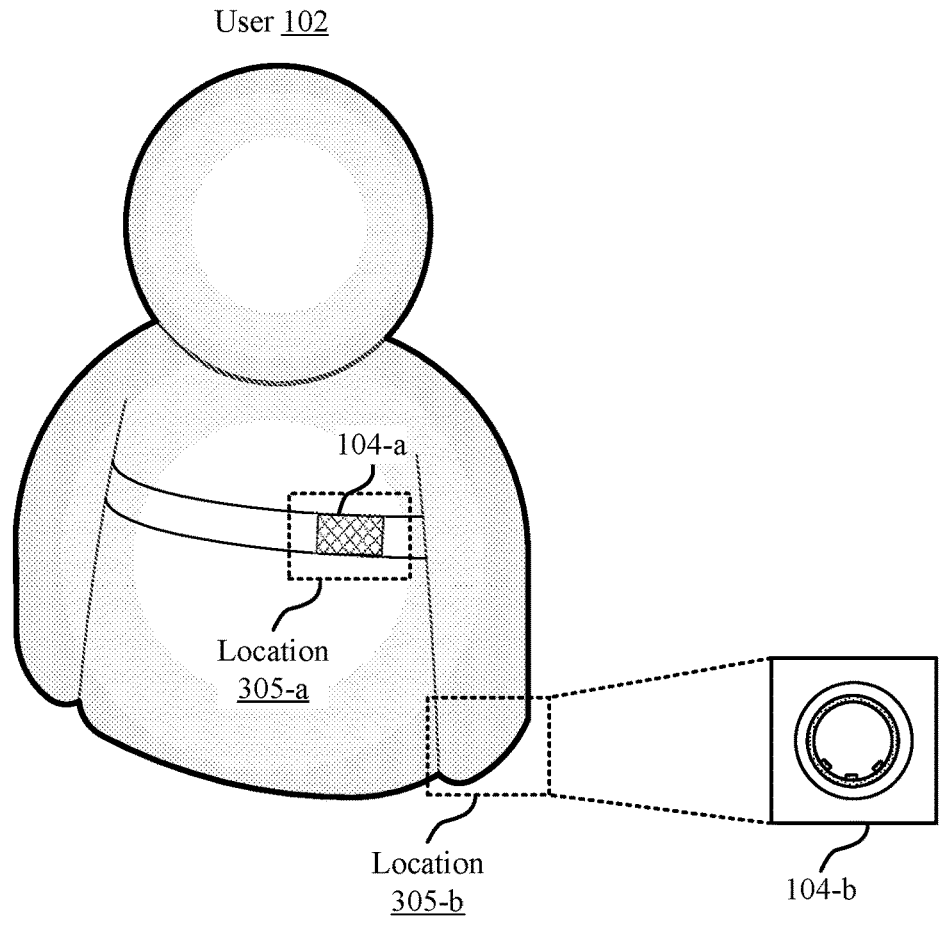
FIG. 3 shows an example of a multiple wearable device system that supports techniques for determining blood pressure based on a relative timing of pulses in accordance with aspects of the present disclosure.
Figure 3:
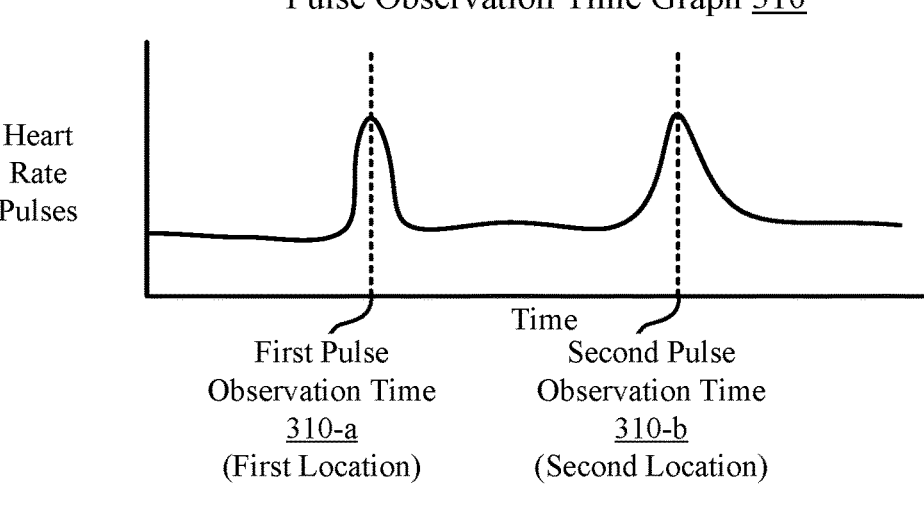

FIG. 3 illustrates an example of a multiple wearable device system 300 that supports techniques for determining blood pressure based on a relative timing of pulses in accordance with aspects of the present disclosure. In some implementations, the multiple wearable device system 300 may implement, or be implemented by, aspects of the system 100 and the system 200 as described with reference to FIGS. 1 and 2. For example, the multiple wearable device system 300 may be implemented by a wearable device 104 (e.g., a ring 104), a user device 106, one or more servers 110, or any combination thereof.

In the following description of the multiple wearable device system 300, the operations may be performed in a different order than the example order shown, or the operations may be performed in different orders or at different times. Some operations may also be omitted from the multiple wearable device system 300, and other operations may be added to the multiple wearable device system 300. In this example, the multiple wearable device system 300 may be referred to as a system 300. Accordingly, the terms "a first wearable device 104-a," "a second wearable device 104-b," and like terms, may be used interchangeably with "a wearable ring device," unless noted otherwise herein.

In the example of FIG. 3, the system 300 may use multiple wearable devices 104 (e.g., chest-worn wearable devices, wearable ring devices, wearable watches) placed at different locations of the body (e.g., chest, finger, wrist, ankles, or the like) to determine blood pressure metrics for the user 102. In this example, the user 102 may wear the first wearable device 104-a at a location proximate to a chest of the user 102 (e.g., a first physiological location, a first location 305-a) and the second wearable device 104-b at a location on an extremity (e.g., finger, hand, wrist, foot, ankle) of the user 102 (e.g., a second physiological location, a second location 305-b) for the system 300 to acquire respective physiological data from the user 102. That is, one or more heartbeats propagate from the user's 102 heart to different (e.g., distal) locations of the body (e.g., fingers, toes, the head, and the like) of the user 102. In this example, the one or more heartbeats may be used interchangeably with one or more pulses.

As described previously herein, heartbeat pulses may propagate to different locations 305 of the body at varying speeds based on the variable blood pressure of the user 102. For example, a higher blood pressure may cause heartbeats to propagate throughout the body at a faster rate, while a lower blood pressure may cause heartbeats to propagate throughout the body at a faster rate. That is, fluctuating blood pressures with according speeds may result in pulses reaching different locations 305 at different times.

In some cases, the system 300 may acquire physiological data, such as first physiological data and second physiological data, from the wearable devices 104. In some implementations, the system 300 may acquire physiological data that includes one or more heartbeat pulses of the user 102 and may compare pulses over a time period. In some examples, the system 300 may acquire first physiological data from the user 102 via the first wearable device 104-a that indicates a first pulse observation time 310-a of a heartbeat of the user 102 at the first location 305-a, and second physiological data from the user 102 via the second wearable device 104-b that indicates a second pulse observation time 310-b of the heartbeat (or an additional heartbeat) of the user 102 at the second location 305-b. In some cases, the first pulse observation time 310-a and the second pulse observation time 310-b may indicate when a heartbeat (or separate heartbeats) arrive at (e.g., are observed at) the respective locations 305.

In some cases, the pulse observation times 310 may be used to determine time periods that that it takes for heartbeat pulses to travel between different locations of the user's body (e.g., time it takes for a heartbeat to travel from the heart at the first location 305-a to the second location 305-b). That is, the user 102 may wear multiple wearable devices 104 at different locations 305. In this example, the wearable device 104-a is located at a location 305-a worn on the chest of the user 102 and the wearable device 104-b is worn on the finger of the user 102. However, in other examples, the wearable devices 104 may include a wearable device 104 (not illustrated) worn on the wrist of the user 102 (e.g., a wearable watch) at the first location 305-a and the wearable device 104-b worn on the finger of the user 102 at the second location 305-b.

In these examples and additional examples, the system 300 may measure pulse observation times 310 that indicate when the heartbeat arrives at the different locations 305. In some examples, the system 300 may determine that the first pulse observation time 310-*a* at the first location 305-*a* is recorded at a time before the second pulse observation time 310-*b* at the second location 305-*b*. That is, the second pulse observation time 310-*b* may occur subsequent to the first pulse observation time 310-*a* due to the additional time necessary for the one or more pulses to travel from the heart to the second location 305-*b*. In such examples, the system 300 may record different pulse observation times 310 for one heartbeat at different wearable devices 104 depending on the location 305 of the wearable devices 104 relative to the heart of the user 102.

In some examples, the pulse observation times 310 may include measurements of time, specifically PTTs and PATs that indicate the time that elapses for a pulse to reach different locations of a body of one or more users 102. That is, a PTT may indicate a time period for a pulse to travel from one arterial site to another arterial site (e.g., a time difference between pulse arrival times for two peripheral site PPGs). In other examples, a PAT may indicate a time interval for a pulse wave to travel from the heart of the user 102 to one or more distal places on the body. That is, the PAT may consider the PTT in addition to the pre-ejection period (PEP), where the PEP is a time period where no blood is ejected in addition to the time necessary to convert the electrical signal into a mechanical pumping force and the isovolumetric contraction of the left ventricle to open the aortic valve in the heart of the user 102. In some examples, pulse observation times 310 may be compared to estimate an accurate blood pressure of the user 102. For example, the system 300 may compare a PTT that may represent the first pulse observation time 310-*a* at the first location 305-*a* and a PAT that may represent a second observation time 310-*b* at the second location 305-*b* to estimate blood pressure for the user 102. As such, the system 300 may observe multiple pulse observation times 310 to determine when one or more pulses arrive at different parts of the body of the user 102 (e.g., ECG at the heart to the PPG pulse at the finger, or PPG at the wrist then the finger).

Upon determining pulse observation times 310, the system 300 may determine a pulse time (e.g., PTT, PAT, a time difference of pulses) associated with the one or more heartbeat pulses. That is, the system 300 may compare the respective pulse observation times 310, such as a comparison between the first pulse observation time 310-*a* and the second observation time 310-*b*, to determine a blood pressure metric for the user 102. In some examples, the system 300 may determine the pulse time as a time interval between the first pulse observation time 310-*a* and the second pulse observation time 310-*b*. As such, the system 300 may utilize multiple wearable devices 104 that are worn at different locations 305 and may compare the time interval between the observation times 310 to determine when pulses are detected at the different locations 305 to determine the blood pressure metric for the user 102.

While FIG. 3 illustrates different wearable devices 104-*a*, 104-*b* located proximate to the user's heart and the user's hand/finger, this is solely for illustrative purposes. In this regard, aspects of the present disclosure may be used to compare pulse observation times 310 between any two locations 305 of the user's body, and therefore measure pulse times (e.g., PTTs, PATs) between any two locations 305. For example, in other cases, the system 300 may measure pulse observation times 310 between wearable devices 104 worn on each hand, between wearable devices worn on the user's wrist and the user's finger, etc. In such cases, the pulse observation times 310 may be used to determine blood pressure metrics for the user.

Additionally, or alternatively, the system 300 may use a combination of wearable devices and other devices (e.g., camera or microphone of a user device 106) placed at different locations of the body (e.g., chest, finger, wrist, ankles, or the like) to determine physiological metrics for the user 102. For example, the user 102 may hold a user device 106 up to their chest (e.g., location 305-*a*) so that a microphone or other audio component of the user device 106 can collect audio data (e.g., sound data, sound pulses) that are used to determine when the user's heart beats. Similarly, the wearable ring device 104-*b* may measure when the heartbeats arrive at the user's finger. In this regard, the microphone of the user device 106 may be used to determine a first pulse observation time 310-*a* at the first location 305-*a* (e.g., chest), and the wearable ring device 104-*b* may be used to determine a second pulse observation time 310-*b* at the second location 305-*b* (e.g., finger). The pulse observation times 310-*a*, 310-*b* may then be used to determine PTTs and/or other physiological metrics, such as PWV, blood pressure, arterial stiffness, arterial plaque, cardiovascular age metrics, and the like.

Figure 4:
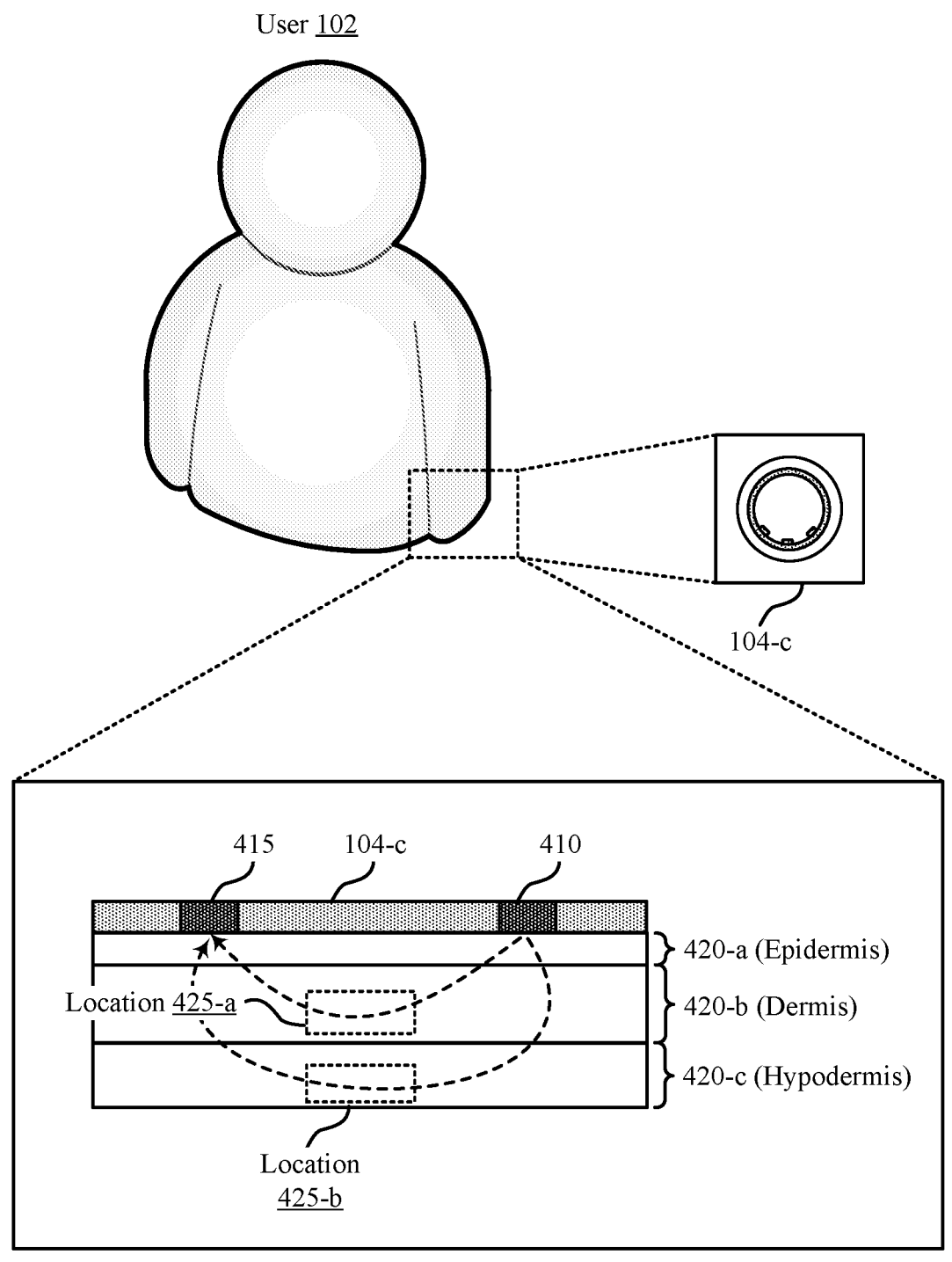
FIG. 4 shows an example of a wearable device system that supports techniques for determining blood pressure based on a relative timing of pulses in accordance with aspects of the present disclosure.

FIG. 4 illustrates an example of a wearable device system 400 that supports techniques for determining blood pressure based on a relative timing of pulses in accordance with aspects of the present disclosure. In some implementations, the wearable device system 400 may implement, or be implemented by, aspects of the system 100, the system 200, and the system 300, as described with reference to FIGS. 1-3.

For example, the wearable device system 400 may be implemented by a wearable device 104 (e.g., a ring 104), a user device 106, one or more servers 110, or any combination thereof. In the following description of the wearable device system 400, the operations may be performed in a different order than the example order shown, or the operations may be performed in different orders or at different times. Some operations may also be omitted from the wearable device system 400, and other operations may be added to the wearable device system 400. In this example, the wearable device system 400 may be referred to as a system 400. Accordingly, the term "a wearable device 104-*c*" may be used interchangeably with "a wearable ring device," unless noted otherwise herein.

In the example of FIG. 4, the system 400 may use a single wearable device 104-*c* to determine a blood pressure metric for the user 102 based on when pulses arrive at different tissue layers 420. For example, the wearable device 104-*c* may use PPG techniques that include a triple LED (e.g., red, green, and IR) system that enables the wearable device 104-*c* to propagate multiple light waves into different tissue layers 420 of the user 102 based on the wavelength of light. That is, the penetration depth of light into the skin of the user 102 increases with wavelength from the UV to the visible light range and through the IR range.

In the system 400, a light emitting component 410 (e.g., LED) and a photodetector 415 may be coupled to a controller to transmit light to locations 425 associated with one or more wavelengths and acquire measurements. In other words, different wavelengths of light (and/or different pressures applied to the wearable device 104-*c*) may be used to transmit light to different tissue penetration depths in order to determine pulse observation times (e.g., pulse observation times 310 as shown in FIG. 3) at different locations 425.

In this example, the light emitting component 410 may transmit first light (not illustrated) associated with a wavelength range that penetrates to a depth or location 425-*a* at the epidermis layer 420-*a*, where the first light travels back to the photodetector 415 with acquired first physiological data. Additionally, the light emitting component 410 may transmit second light associated with a wavelength range that penetrates to a depth or location 425-*b* at the hypodermis layer 420-*c*, where the second light travels back to the photodetector 415 with acquired second physiological data. That is, the system 400 may enable the controller of the wearable device 104 to transmit a blue light that travels up to 460 nm, a green light associated with a wavelength of approximately 530 nm, a red light associated with a wavelength of approximately 660 nm, and/or an IR light associated with a wavelength of approximately 940 nm, where each of the transmitted wavelengths of light may reach one or more tissue layers 420 (e.g., an epidermis layer 420-*a* at around 0.3 millimeters (mm), a dermis layer 420-*b* at around 1.0 mm, a hypodermis layer 420-*c* at around 3.0 mm). That is, each of the transmitted lights may reach the one or more layers of tissues where the blood vessels are located, such as the capillaries located closest to the skin of the user 102 at the epidermis, the arterioles located at the middle layer at the dermis, and the arteries located at the deepest layer at the hypodermis. As such, the system 400 may use a light emitting component 410 and photodetector 415 coupled to a controller on the wearable device 104-*c* to transmit one or more lights associated with wavelength ranges to one or more tissue layers 420 at multiple locations 425 to acquire physiological data.

Further, the single wearable device 104-*c* may transmit light from the light emitting component 410 through one or more tissue layers 420 and back to the photodetector 415 to acquire first physiological data from the user 102. In some examples, the first physiological data may indicate a first pulse observation time of a heartbeat of the user 102 at a first tissue penetration depth (e.g., the epidermis layer 420-*a*, the dermis layer 420-*b*). In addition, the wearable device 104-*c* may acquire a second physiological data from the user 102, where the second physiological data may indicate a second pulse observation time of the heartbeat, an additional heartbeat of the user, or both at a second tissue penetration depth (e.g., the dermis layer 420-*b*, at the hypodermis layer 420-*c*). In some examples, the system 200 may determine that heartbeat pulses arrive faster at one or more arteries located at the second layer, such as the dermis layer 420-*b* or the hypodermis layer 420-*c*, and heartbeat pulses arrive later at one or more capillaries located at the first layer, such as the epidermis layer 420-*a*, or vice versa.

As such, the system 400 may determine a pulse time associated with the heartbeat, the additional heartbeat, or both, based on a comparison between the first pulse observation time and the second pulse observation time. Further, the system 400 may use the pulse time to determine a blood pressure metric for the user 102. In other words, the system 400 may determine a difference between when heartbeat pulses are observed at different layers of tissue or different penetration depths to determine a blood pressure metric for the user. Thus, the system 400 may use a single wearable device 104-*c* to measure the time that elapses for pulses to reach different tissue penetration depths for determining the blood pressure of the user 102.

In some cases, light emitted by light-emitting components 410 of the wearable device 104-*c* (e.g., LEDs) may be measured by multiple photodetectors 415. In some cases, the light-emitting components 410 and photodetectors 415 may be positioned at different radial positions on an inner circumferential surface of the wearable device 104-*c*. For example, in some cases, multiple light-emitting components 410 and multiple PDs may be arranged around the inner circumferential surface of the wearable device 104-*b* in in an interleaving pattern (e.g., LED, PD, LED, PD) at regular or irregular spacings between the respective components. In other cases, multiple photodetectors 415 may be positioned adjacent to one another at a same or similar radial position of the wearable device 104-*c*.

In some cases, measuring light with multiple photodetectors 415 (e.g., multiple photodetectors 415 that are the same distance away from a common light-emitting component 410) may enable the wearable device 104-*c* to determine phase differences in light signals received at the respective photodetectors 415. Such parallel measurement of light by multiple photodetectors 415 may enable more robust and reliable PPG data collection. For example, in some cases, phase differences between light measured at multiple PDs 315 may be used to determine a velocity of blood moving throughout the blood vessels, which may be used to further determine or estimate blood pressure.

As described previously herein, aspects of the present disclosure may utilize PPG data to identify pulse observation times, and may thereby use PPG data to determine blood pressure metrics for a user. In some implementations, a wearable device 104 may collect PPG data in the form of one or more sets of PPG pulses to measure specific physiological parameters of the user. However, not all PPG pulses may exhibit the same morphological features or characteristics. In other words, PPG pulses may exhibit varying shapes and characteristics. That is, morphological features of PPG pulses (e.g., PPG pulse amplitude, duration, slope, curvature, relationships between peaks) may vary from one PPG pulse to the next, and some of the PPG pulses may inaccurately represent a physiological measurement. Additionally, or alternatively, factors such as light, pressure, a posture of the user (e.g., the user is sitting or standing), or a hydration of the user (e.g., the user may have swollen fingers due to lack of hydration) may affect the accuracy of the PPG data. In particular, a system that uses the inaccurate PPG pulses or fails to account for additional factors that affect the PPG data may result in unreliable physiological measurements. That is, multiple systems may benefit from one or more techniques for identifying PPG pulses that accurately represent the physiological metrics of one or more users.

Accordingly, in some implementations, the systems 100, 200, 300, 400 of the present disclosure may be configured to identify one or more "representative" (e.g., common, average) PPG pulses that accurately represents the physiological metrics of the user, and may utilize identified, representative PPG pulses to determine pulse observation times and/or blood pressure measurements. That is, techniques described herein may be used to identify the PPG pulses that are of high quality and accurately reflect physiological metrics of the user in order to determine blood pressure measurements.

To identify the one or more PPG pulses that accurately represents the physiological metrics of the user (e.g., identify PPG pulses that will be used to determine pulse observation times and/or blood pressure metrics), a wearable device 104 may acquire PPG data that includes a first set of PPG pulses from the user. In some aspects, the system may compare multiple morphological features from the first set of PPG pulses for each specific physiological measurement. Further, the system may determine one or more PPG profiles (e.g., one or more representative PPG pulses, one or more common pulse templates) for each specific physiological metric based on the comparison of the multiple morphological features of the first set of PPG pulses. That is, each of the one or more PPG profiles may include a set of multiple morphological value ranges for the multiple morphological features. In some examples, each of the PPG profiles may represent a representative (e.g., common, average) pulse calculated from the first set of PPG pulses for each specific physiological measurement.

In addition, the system may acquire additional PPG data from the user via the wearable device 104. In some cases, the system may acquire the additional PPG data from the user as a second set of PPG pulses. In some implementations, the system may determine that one or more PPG pulses from the second set of PPG pulses match the one or more PPG profiles from the first set of PPG pulses. That is, the system may detect that multiple morphological feature values of the second set of PPG pulses satisfy the multiple morphological value ranges of the one or more PPG profiles. In other words, the system may identify which PPG pulses of the second set of PPG pulses "match" the PPG profiles.

Subsequently, the system may determine one or more physiological metrics associated with the user based on the one or more PPG pulses from the second set of PPG pulses matching the one or more PPG profiles from the first set of PPG pulses. Stated differently, the system may utilize the PPG pulses that "match" the PPG profiles (e.g., the system may utilize "representative" PPG pulses) to perform physiological measurements for the user. For example, the system/wearable device 104 may be configured to utilize PPG pulses that match the PPG profiles to determine pulse observation times, and therefore determine blood pressure measurements.

Conversely, the system may detect that the one or more PPG pulses from the second set of PPG pulses fails to match the one or more PPG profiles from the second set of PPG pulses and may refrain from using that specific physiological metric associated with the user or otherwise take this information into account. In other words, the system/wearable device may not utilize PPG pulses that do not match PPG profiles to determine pulse observation times and/or blood pressure measurements.

In some aspects, the wearable device may identify the one or more representative PPG pulses for each user using the existing hardware features of the wearable device. In some examples, the system may define the one or more PPG pulse profiles (e.g., one or more PPG templates) that represent common PPG pulses of the user. That is, the system may acquire one or more PPG pulses and may compare each of the PPG pulses to each other to determine the one or more PPG pulse profiles. In such cases, the system may determine the one or more PPG profiles by identifying common (e.g., average) values (e.g., average length, amplitude, slope, or the like) of the multiple PPG pulses. For example, the system may define one or more PPG pulse profiles based on common PPG pulses acquired from the user via a day-time calibration sequence. That is, the calibration sequence may be initiated to define valid samples to determine which of the PPG pulses are suitable (e.g., reliable) for performing physiological measurements. In some cases, the system may utilize a changing correlation between different signal paths to find an optimal measurement time for the PPG pulses.

In some implementations, the system may account for posture estimation of the user, and may determine different sets of PPG profiles based on different postures of the user. For example, the system may detect the posture of the user (e.g., the user may be standing, sitting, lying down, or the like) which may affect the signal quality metrics of the PPG pulses. As such, the system may use the PPG pulse profiles, the calibration sequence, and additional factors to select accurate PPG pulses with appropriate signal quality metrics that represent the physiological metrics of the user (e.g., first set of PPG profiles for when the user is standing, and second set of PPG profiles for when the user is sitting).

Figure 5:
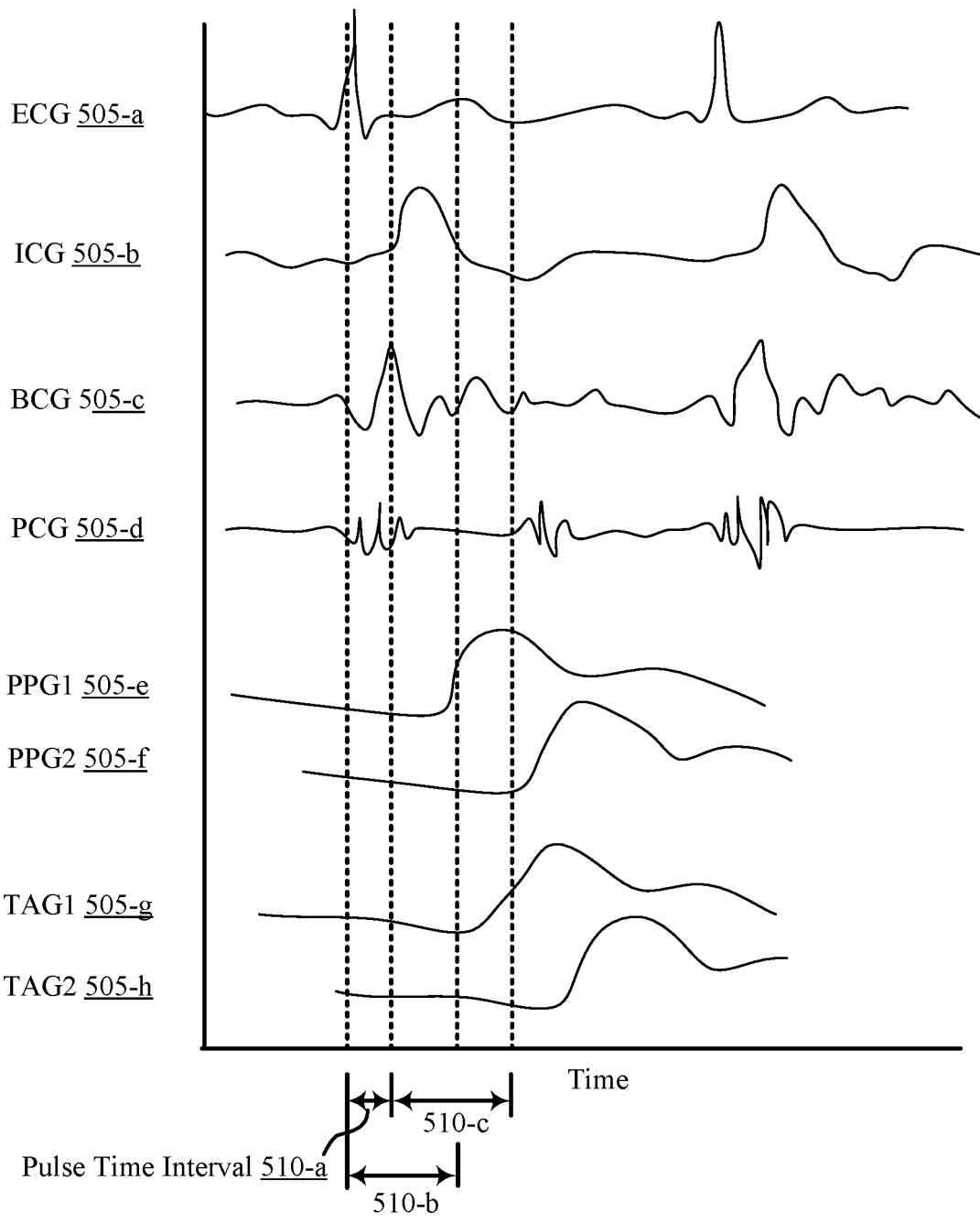
FIG. 5 shows an example of a timing diagram that supports techniques for determining blood pressure based on a relative timing of pulses in accordance with aspects of the present disclosure.

FIG. 5 illustrates an example of a timing diagram 500 that supports techniques for determining blood pressure based on a relative timing of pulses in accordance with aspects of the present disclosure. In some implementations, the timing diagram 500 may implement, or be implemented by, aspects of the system 100, the system 200, the system 300, and the system 400 as described with reference to FIGS. 1-4.

For example, the timing diagram 500 may represent one or more cardiac measurements of a user, such as a user 102 where the cardiac measurements are acquired using a wearable device (e.g., a wearable device 104, a blood pressure device, a sphygmomanometer, a blood pressure cuff, a blood pressure monitor). In the following description of the timing diagram 500, the cardiac measurements may be performed in a different order than the example order shown, or the cardiac measurements may be performed in different orders or at different times. Some cardiac measurements may also be omitted from the timing diagram 500, and other cardiac measurements may be added to the timing diagram 500.

In the example of FIG. 5, the timing diagram 500 may represent multiple cardiac measurements over a period of time. In some examples, the user may be equipped with one or more devices (e.g., one or more wearable devices 104, one or more blood pressure devices) to study cardiac measurements of the user. In some examples, the timing diagram 500 may represent multiple curves 505 as a graphic recording of the movement, or a function of the heart that may be used for a diagnosis of the user. That is, the timing diagram 500 may be used to illustrate cardiac time intervals that provide information about the user's left ventricular performance. For example, in the example of FIG. 5 the one or more devices may conduct an ECG test, where an electrical signal from the heart of the user is checked for heart conditions and one or more pulse observation times may be monitored.

In some aspects, the timing diagram 500 may depict an ECG curve 505-*a* with one or more pulse observation times, such as PTTs and PATs that indicate the time that elapses for a pulse to reach different locations of a body for the user. That is, a PTT may indicate a time period for a pulse to travel from one arterial site to another arterial site (e.g., a time difference between pulse arrival times for two peripheral site PPGs). In other examples, a PAT may indicate a time interval for a pulse wave to travel from the heart of the user to one or more distal places on the body. That is, the PAT may consider the PTT in addition to the PEP, where the PEP is a time period where no blood is ejected in addition to the time necessary to convert the electrical signal into a mechanical pumping force and the isovolumetric contraction of the left ventricle to open the aortic valve in the heart of the user. In some examples, the PEP may affect the cardiac measurements represented in the timing diagram 500.

Additionally, the timing diagram 500 may depict an impedance cardiography (ICG) measurement represented as an ICG curve 505-*b* that measures cardiac function (e.g., cardiac output, cardiac index, stroke volume, and stroke volume index) of the heart. That is, the ICG curve 505-*b* may represent the mechanical function of the heart and may measure the total electrical conductivity of the thorax, where the thorax is an area of the body between the neck and the abdomen of the user.

Further, the timing diagram 500 may depict a ballistocardiograph (BCG) measurement represented as an BCG curve 505-c that measures ballistic forces generated by the heart. That is, the BCG curve 505-c may represent the downward movement of blood through a descending aorta of the user. The downward movement of blood may produce an upward recoil that moves the body of the user upward with each heartbeat. As such, the timing diagram 500 may include the BCG curve 505-c to show mechanical vibrations caused by cardiac activity of the user.

In addition, the timing diagram 500 may depict a phonocardiogram (PCG) measurement represented as a PCG curve 505-d that measures heart sounds. In some examples, the PCG curve 505-d may represent sounds and murmurs created by the closure of multiple heart valves. That is, the PCG curve 505-d may represent two dominant sounds, such as S1 and S2 in rhythmical form. The S1 may represent when the atrioventricular valves (e.g., tricuspid valves, mitral valves) close at the beginning of a systole, where the systole represents the phase of the heartbeat when the heart muscle contracts and pumps blood from the chambers into the arteries, and the S2 may represent when the aortic valve and pulmonary valve (e.g., semilunar valves) close at the end of the systole. As such, the timing diagram 500 may include the PCG curve 505-d to determine if the user has a heart murmur that may affect the overall health of the user.

In some aspects, the timing diagram 500 may include one or more PPG curves, such as a PPG1 curve 505-e and a PPG2 curve 505-f, that represent volumetric variations of blood circulation for the cardiovascular system of the user. In some examples, the PPG1 curve 505-e and the PPG2 curve 505-f may represent a one or more pulses of a user and the respective time that elapses for the one or more pulses to reach a different location. That is, the PPG1 curve 505-e may represent the PPG pulse at a first location (e.g., a chest area of the user, a first tissue layer of the user) and the PPG2 curve 505-f may represent the PPG pulse at a second location (e.g., an extremity of the user, a second tissue layer of the user). As such, the timing diagram 500 may represent a difference in time between the PPG pulse represented in PPG1 curve 505-e versus the PPG pulse represented in the PPG2 curve 505-f.

In some examples, the timing diagram 500 may depict one or more tags (e.g., identifiers), such as a TAG1 curve 505-g and a TAG2 curve 505-h that tracks myocardial motion. That is, the myocardium facilitates the contraction and relaxation of the heart walls in order to receive and pump the blood into the systemic circulation of the user. That is, one or more tags may be defined upon detection of a QRS complex (e.g., wave), where the QRS complex represents the depolarization of ventricles of the ECG. That is, the one or more tags may be based on the ECG curve 505-a and may reflect underlying myocardial deformation. As such, the one or more tags may indicate the viability of the muscles of the heart of the user.

In some implementations, the one or more devices may compare pulse timings associated with one or more curves 505 to obtain one or more pulse time intervals 510. In some examples, pulse timings may include pulse observation times, PTTs, PATs, and/or PEPs. That is, each of the pulse time intervals 510, such as a pulse time interval 510-a, a pulse time interval 510-b, and a pulse time interval 510-c, as well as additional pulse time intervals (not illustrated) may indicate respective timing intervals useful for determining cardiac measurements and subsequently blood pressure of the user.

Figure 6:
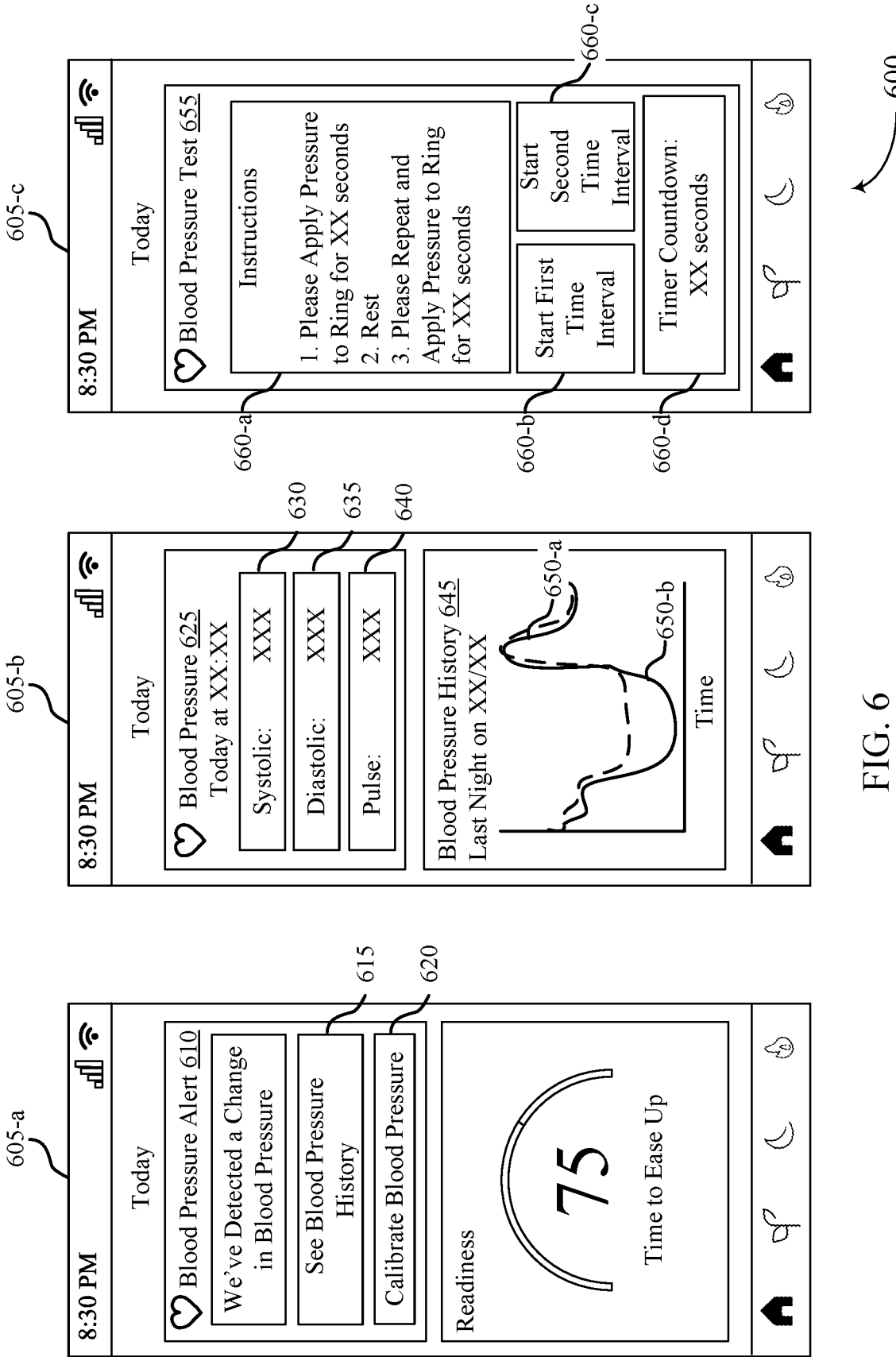
FIG. 6 shows an example of a graphical user interface (GUI) that supports techniques for determining blood pressure based on a relative timing of pulses in accordance with aspects of the present disclosure.

FIG. 6 illustrates an example of a GUI 600 that supports techniques for determining blood pressure based on a relative timing of pulses in accordance with aspects of the present disclosure. The GUI 600 may implement, or be implemented by, aspects of the system 100, the system 200, the system 300, the system 400, the timing diagram 500, or any combination thereof. For example, the GUI 600 may be implemented for a user at a user device connected to a wearable device (e.g., a wearable ring device, watch, necklace, or any other wearable device), and that may be examples of a user 102, a user device 106, and a wearable device 104 as described with reference to FIGS. 1-5.

The GUI 600 illustrates a series of application pages, including an application page 605-a, an application page 605-b, and an application page 605-c, that may be displayed to a user via the GUI 600 (e.g., a user 102 and a GUI 275 as described with reference to FIGS. 1-5). In some examples, the user may open the application page 605-a to see scores belonging to the user. For example, the application page 605-a may display a Sleep Score, a Readiness Score, and the like. In some examples, the application page 605-a may illustrate a blood pressure alert 610 that shows alerts for the user. For example, the blood pressure alert 610 may indicate that a change of blood pressure of the user was detected. That is, the user may select a blood pressure history 615 of the user. Additionally, or alternatively, the user may decide that blood pressure measurements for the user may need to be calibrated again. That is, the user may have experienced a change that has affected blood pressure metrics. For example, the user may have traveled to a higher elevation and is experiencing swollen extremities (e.g., fingers) due to dehydration. Further, the user may select a box to calibrate blood pressure to enable the wearable device to acquire accurate blood pressure metrics.

In some examples, the user may select the blood pressure history 615 feature and the application page 605-b may appear on the user device. The application page 605-b may show a blood pressure 625 acquired at the current day and a specific (e.g., current) time. In some examples, the blood pressure 625 may depict several measurements, such as a systolic blood pressure 630 measured from one or more arteries when the user's heart beats and a diastolic blood pressure 635 measured from one or more arteries when the heart is in between heart beats. In some examples, a classification of blood pressure may include either a normal blood pressure or a high blood pressure. For the user, a normal blood pressure may indicate a systolic blood pressure of less than 130 mmHg and a diastolic blood pressure of less than 80 mmHg. Alternatively, a high blood pressure may indicate a systolic blood pressure greater than 130 mmHg and a diastolic blood pressure greater than 80 mmHg. Additionally, a pulse 640 may be displayed and represents a measurement of heart rate (e.g., number of times the heart of the user beats per minute). Further, the pulse 640 may be calculated by subtracting the diastolic blood pressure 635 from the systolic blood pressure 625.

Additionally, or alternatively, the application page 605-b may illustrate a blood pressure history 645 of the user for a specific term. In the example of FIG. 6, the blood pressure history 645 depicts a night term for a specific date with two trendlines. That is, the blood pressure history 645 may illustrate a baseline (e.g., normal, typical, trend) blood pressure metric 650-a associated with the user and a blood pressure metric 650-b for the night term at the specific date.

That is, application page 605-*b* of the user device may graphically illustrate comparisons between the blood pressure metric 650-*a* that represents typical blood pressure trends for a night of the user to the blood pressure metric 650-*b* that represents the blood pressure trends for the last night term of the user. That is, the GUI 600 may display and/or indicate information associated with the difference between the baseline blood pressure metric 650-*a* and the blood pressure metric 650-*b* (e.g., your blood pressure is ±X compared to your average blood pressure).

In some examples, the GUI 600 may share information that may be indicative of whether the user has nocturnal hypertension based on a dipping of pulses. For the user, a normal, nocturnal blood pressure trend may indicate a blood pressure dipping about 10% to 15% less than typical daytime pulses. However, detecting blood pressure changes (e.g., blood pressure changes based on absolute values and additional values) greater than 15% may indicate a warning that the user has an elevated sodium level, a salt sensitivity, CKD, CHF, diabetes, a structural vascular disease, insomnia, or the like. That is, the user may look at the blood pressure history 645 over time periods to determine whether blood pressure metrics 650 may point to possible cardiovascular health risks.

In some examples, the user may select the blood pressure calibration 620 feature and the application page 605-*c* may appear on the user device. In such examples, the user may select the blood pressure calibration 620 feature and may undergo a blood pressure test 655. That is, the application page 605-*c* may indicate that the user may take the blood pressure test 655 and to follow a set of instructions. For example, an instruction box 660-*a* may indicate for the user to apply pressure to the wearable device (e.g., press against the wearable device, clench fists to apply pressure to a wearable ring) for an interval of time, to rest (e.g., pause) and not apply pressure to the ring to lower the pressure to a normative state, and to again apply pressure to the wearable device for another interval of time. Further, the blood pressure test 655 may display two time interval boxes, such as a start first time interval 660-*b* box and a start second time interval 660-*c* box, that enables the user to start the time interval periods for applying pressure to the wearable device. That is, a timer countdown 660-*d* box may indicate a time period in seconds for the user to apply the first pressure and the second pressure, or a time period in seconds for the user to rest in between time intervals. In some examples, the blood pressure test 655 may enable a system with a single wearable device to monitor pulse observation times of different pulses at variable tissue penetration depths. As described previously herein, the application of different pressures over different time intervals may enable the wearable device to observe heartbeat pulses at different tissue penetration depths, thereby enabling blood pressure measurements.

Figure 7:
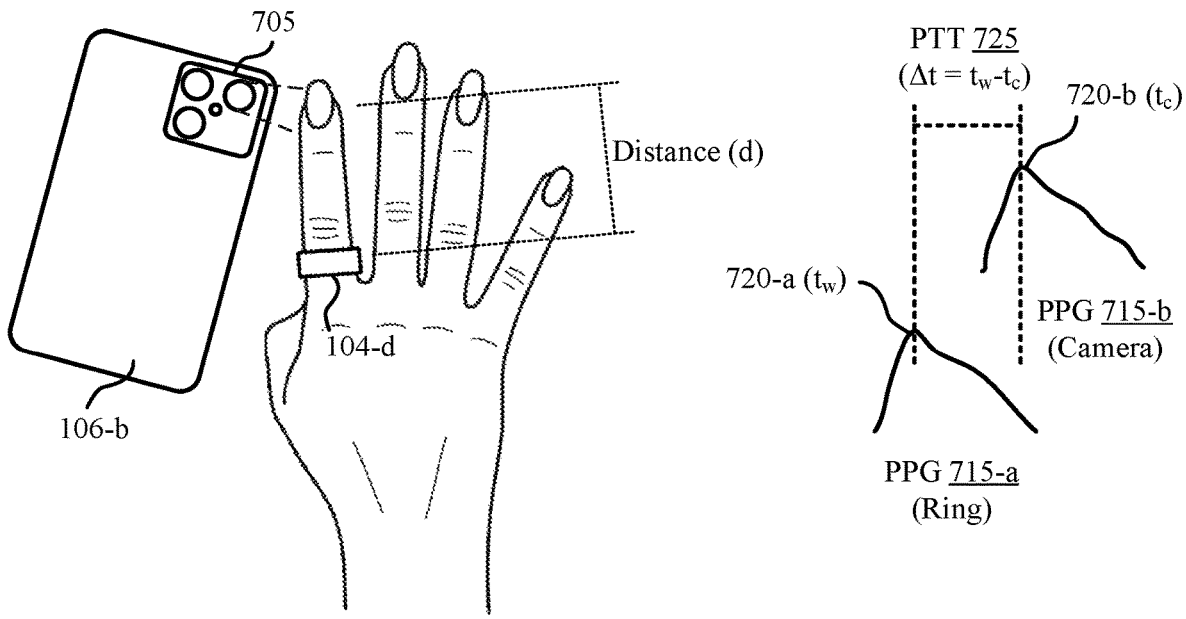
FIG. 7 shows an example of a system that supports techniques for determining blood pressure based on a relative timing of pulses in accordance with aspects of the present disclosure.

FIG. 7 illustrates a system 700 that supports techniques for determining blood pressure based on a relative timing of pulses in accordance with aspects of the present disclosure. Aspects of the system 700 may implement, or be implemented by, aspects of the system 100, the system 200, the system 300, the system 400, the timing diagram 500, the GUI 600, or any combination thereof. In particular, the system 700 illustrates techniques for a "blood pressure spot check" used to estimate blood pressure metrics for a user based on PTTs determined using a wearable device 104-*d* and an imaging device 705, including techniques for synchronizing or calibrating internal clocks of the wearable device 104-*d* and the imaging device 707.

In some implementations, the system 700 may be configured to determine blood pressure metrics for a user by using a wearable device 104-*d* and an imaging device 705. In particular, the wearable device 104-*d* and the imaging device 705 may be used to determine pulse observation times 720 of heartbeats at different physiological locations of the user's body, where the pulse observation times 720 may be used to determine PTTs that are used to estimate blood pressure.

For example, as shown in FIG. 7, the system 700 may include a wearable device 104-*d* (e.g., wearable ring device 104-*d*) that is configured to acquire physiological data (e.g., PPG data 715-*a*) at a first physiological location, namely, at the base of the user's finger. Additionally, the system 700 may include an imaging device 705 that is configured to acquire physiological data (e.g., PPG data 715-*b*) by taking images (e.g., video stream) at a second physiological location, namely, at the user's fingertip (e.g., the fingertip of the same finger that includes the wearable device 104-*d*). In some aspects, processors within the system 700 (e.g., processors within the wearable device 104-*d*, imaging device 705, user device 106-*b*, servers 110, etc.) may be configured to extract PPG data 715-*b* from images/video taken by the imaging device 705 by utilizing one or more algorithms (e.g., machine learning models) that are configured to convert two-dimensional (2D) image data into one-dimensional (1D) PPG data. For instance, images/video taken by the imaging device 705 may exhibit different colors or intensities of particular wavelengths as the blood vessels in the user's fingertip expand and contract based on the user's heartbeat pulses. In such cases, the system 700 may utilize one or more algorithms to convert an intensity of particular wavelengths (e.g., intensity of red wavelengths) within the 2D data of the collected images to PPG data 715-*b* that illustrates a changing intensity of the respective wavelengths over time.

In some cases, as shown in FIG. 7, the imaging device 705 may be part of, or included within, a user device 106-*b* associated with the wearable device 104-*d*. Moreover, in some cases, the imaging device 705 may include a light source that is configured to project light into the user's tissue to help the imaging device 705 identify pulse observation times 720 of heartbeat pulses. Further, in some cases, the imaging device 705 may include another wearable device (e.g., wrist-worn wearable device, another wearable ring device, etc.). As such, techniques described herein may be utilized to synchronize internal clocks and/or collected physiological data across multiple different devices, such as the wearable device 104-*d* and the imaging device 705, between multiple wearable devices 104, and the like.

Together, the wearable device 104-*d* and the imaging device 705 may be used to perform a "blood pressure spot check" to estimate the user's blood pressure. In this example, the wearable device 104-*d* may be configured to determine when heartbeat pulses arrive at the base of the finger (e.g., first pulse observation time 720-*a* ($t_w$)), and the imaging device may be configured to determine when heartbeat pulses arrive at the fingertip (e.g., second pulse observation time 720-*b* ($t_c$)). In this example, the system 700 may be configured to determine a PTT 725 of the heartbeat pulses (e.g., how long the heartbeat pulses take to travel from the base of the finger to the fingertip), where $PTT = \Delta t = t_w - t_c$. Subsequently, the PTT 725 may be used to determine or estimate a blood pressure metric for the user.

In some cases, the system 700 may be configured to observe multiple pulse observation times 720-*a* at the base of the finger (multiple $t_w$ values) and multiple pulse observation times 720-*b* at the fingertip (multiple $t_c$ values), where the PTT 725 may be determined based on the multiple pulse observation times 720-*a* at the base of the finger (multiple $t_w$ values) and multiple pulse observation times 720-*b* at the fingertip (multiple $t_c$ values). For example, the PTT 725 may be calculated as the average time difference between pulse observation times 720 for each respective heartbeat (e.g., PTT=$\Delta t$=mean($t_{w,i}$−$t_{c,i}$)).

The PTT 725 values may be used to estimate blood pressure values based on the theory that heartbeat pulses take longer to arrive at locations further from the heart, and that higher blood pressure causes heartbeat pulses to travel faster as compared to lower blood pressures. In this regard, the system 700 may be configured to determine blood pressure metrics based on the calculated PTT 725 and the distance (d) between the physiological locations that the pulse observation times 720 were calculated. For example, the system 700 (e.g., wearable device 104-*d*, user device 106-*b*, servers 110) may be configured to calculate a blood pressure metric for the user based on the PTT 725 between the base of the finger and the fingertip, and the distance (d) between the base of the finger and the fingertip. In this regard, because different fingers have different lengths (e.g., different distances (d)), the system 700 may be configured to utilize different mathematical equations and/or different machine learning models in order to calculate blood pressure metrics using PTTs 725 and distances (d) for each respective finger (e.g., first finger has first distance ($d_1$) and a first machine learning model to calculate blood pressure metrics from PTTs 725, and second finger has second distance ($d_2$) and a second machine learning model to calculate blood pressure metrics from PTTs 725).

In additional or alternative cases, a single machine learning model may be used to calculate blood pressure metrics using PTTs 725 on different fingers by utilizing different distance (d) metrics for the respective fingers. In some aspects, the one or more machine learning models may be configured to utilize multiple parameters or variables to calculate blood pressure based on PTT 725, including distance values (d), an age of the user, sex of the user, body mass index (BMI) of the user, the user's baseline blood pressure values, previous diagnosis of hypertension, and the like. In some cases, the user may input (e.g., via the user device 106-*b*) an indication of the distance (d) used to calculate the pulse observation times 720 and PTTs 725. In other cases, the imaging device 705 may be used to capture images or a video of the physiological locations used to determine the pulse observation times 720 and PTTs 725, where the images/video captured by the imaging device 705 may be used to calculate the distance (d).

As noted previously herein, in cases where blood pressure metrics (and/or other physiological metrics) are determined based on PTTs 725, the internal clocks of the respective devices used to determine the pulse observation times 720 and calculate the PTTs 725 must be synchronized, or the data segments aligned. If the internal clocks are even milliseconds off from one another, this results in the PTTs 725 being calculated as milliseconds longer or shorter than reality, which results in inaccurate and unreliable blood pressure metrics.

Accordingly, some aspects of the present disclosure are directed to techniques for synchronizing internal clocks across multiple devices (and/or synchronizing segments of PPG data) that are used to determine pulse observation times 720 and calculate the PTTs 725 that are used to determine physiological metrics, such as blood pressure metrics. In other words, some aspects of the present disclosure are directed to techniques to synchronize or otherwise coordinate the internal clocks of the wearable device 104-*d* and the imaging device 705 in order to improve calculation of PTTs 725, and improve blood pressure determinations.

In particular, in some implementations, the imaging device 705 may keep time based on the internal clock at the user device 106-*b*. In other words, the camera/imaging device 705 may not keep or maintain its own internal clock autonomously, but may rather utilize the internal clock of the user device 106-*b*. In this regard, reference to the internal clock at the imaging device 705 may be understood to refer to the internal clock at the user device 106-*b*. In some aspects, wearable device 104-*d* may periodically sync its time (e.g., internal clock) with the internal clock of the user device 106-*b*. However, different clock rates between the wearable device 104-*d* and the imaging device 705 (resulting from device oscillators at the respective devices) may result in drift between the internal clocks/times at the respective devices. As such, synchronization techniques described herein may help maintain coordination and calibration between the clocks/times at the respective devices, particularly in cases where a relative timing of collected data across the devices is important for determining physiological parameters of the user (such as in the case of determining blood pressure metrics based on PTTs 725). Further, such synchronization techniques for synchronizing internal clocks and/or data collected by the respective devices may be used in contexts beyond PTT 725 and blood pressure measurement, such as in cases for measuring other physiological parameters of the user.

Additionally, or alternatively, aspects of the present disclosure may be used to identify delays between internal clocks at the respective devices, where the determined delays may be used to move or shift segments of PPG data collected during a blood pressure spot check, where the moved/shifted PPG segments may be used to determine PTTs 725 that are used to calculate blood pressure metrics. Each of these respective implementations will be described in further detail herein.

For example, upon initiating a blood pressure spot check (e.g., via a GUI of the user device 106-*d*), the user may be instructed to hold the imaging device 705 so that it is able to take images of the wearable device 104-*d*. The wearable device 104-*d* may be configured to strobe, or flash, LEDs of the wearable device 104-*d* (such as in a predetermined pattern), and the imaging device 705 may be configured to capture one or more images of the flashing/strobing LEDs. In this regard, the system 700 (e.g., processors of the wearable device 104-*d*, user device 106-*b*, imaging device 705, servers 110, or any combination thereof) may be configured to perform a synchronization procedure to identify a delay between internal clocks at the wearable device 104-*d* and the imaging device 705 based on the images of the flashing LEDs captured by the imaging device 705. In particular, the synchronization procedure may be performed to determine when the LEDs were flashed by the wearable device 104-*d*, and when the flashing LEDs were observed by the imaging device 705. The delay determined via the synchronization procedure may then be used to adjust determined pulse observation times 720 (and/or PTTs 725) that are used to estimate blood pressure metrics (and/or other physiological parameters). For instance, the determined delay may be used to synchronize internal clocks at the respective devices. In additional or alternative implementations, the delay may be used to move, shift, or otherwise align segments of PPG data 715 collected during the blood pressure spot check. In such cases, the determined delay may be used to adjust pulse observation times 720 used for the blood pressure spot check, while allowing the wearable device 104-b and imaging device 705 to maintain separate (e.g., unsynchronized) internal clocks and/or clock rates.

For example, the system 700 may be configured to determine a delay between a first time that the LEDs of the wearable device 104-d were flashed, and a second time that the flashing of the LEDs were observed by the imaging device 705 based on the images captured by the imaging device 705. The delay between internal clocks at the respective devices may then be used to "shift" or "stretch" a time axis of PPG data 715 (e.g., shift pulse observation times 720) at one of the devices, where remaining differences between pulse observation times 720 (e.g., remaining PTTs 725) may be used to estimate blood pressure.

For instance, the system 700 may receive/determine a first timestamp indicating a first time that the LEDs were flashed, and may receive/determine a second timestamp indicating a second time that the flashing LEDs were observed by the imaging device 705. In this example, the system 700 may determine a delay between a first internal clock at the wearable device 104-d and a second internal clock at the imaging device 705 based on the received/determined timestamps. Subsequently, the wearable device 104-d and the imaging device 705 may collect the PPG data 715-a, 715-b, and the determined delay may then be used to adjust determined pulse observation times 720 and/or PTTs 725 that are used to estimate blood pressure metrics (and/or other physiological parameters). For instance, the second pulse observation time 720-b observed by the imaging device 705 may be shifted up by the determined delay, and the PTT 725 may be calculated based on the shifted second pulse observation time 720-b.

As described previously herein, the pulse observation times 720 used for the blood pressure spot check may be synchronized/calibrated based on the delay by (1) synchronizing the entire internal clocks/clock rates of the devices (e.g., by shifting the internal clock/clock rate at one of the devices), or (2) by shifting/stretching a segment of PPG data collected during the blood pressure spot check (in which case shifted PPG data would be synchronized/calibrated across the devices, even though the internal clocks/clock rates may not be synchronized across the devices).

The wearable device 104-d and the imaging device 705 may be expected to exhibit a minimum sampling rate to achieve reliable PTTs 725. For example, the wearable device 104-d may be configured to acquire physiological data (e.g., PPG data 715-a) with some minimum sampling rate (e.g., 250 Hz, 500 Hz, etc.). Similarly, the imaging device 705 may be configured to capture images/acquire physiological data (e.g., PPG data 715-b) at some minimum sampling/frame rate (e.g., 60 frames per second (fps), 100 fps, etc.). In some implementations, the system 700 may be configured to synchronize or otherwise coordinate sampling rates (and/or clock rates) at the respective devices based on the synchronization procedure. Synchronizing or otherwise coordinating sampling rates across the devices may be done to ensure that images/data are captured by the respective devices at approximately the same times, or offset relative to one another by some specified amount (e.g., sampling rates may be synchronized or coordinated based on delays between the internal clocks at the respective devices and/or the distance (d) between the devices).

In some aspects, the wearable device 104-d may flash the LEDs during the synchronization procedure with a different (e.g., higher) power level compared to the power level used by the LEDs to acquire physiological data (e.g., PPG data

715-a) from the user. In particular, the power level of the LEDs may be increased when flashing the LEDs during the synchronization procedure so that the imaging device 705 is able to observe the flashing LEDs even while the user continues to wear the wearable device 104-d.

In some cases, a synchronization procedure described herein between the wearable device 104-d and the imaging device 705 may be performed before a blood pressure spot check, after the blood pressure spot check, or both. Performing synchronization procedures before and after each blood pressure spot check may result in multiple separate "synchronization points" that are used to more accurately shift internal clocks (and/or shift/stretch segments of PPG data) for more accurate PTT 725 and blood pressure determinations.

For example, after initiating a blood pressure spot check, the user may be prompted to hold the imaging device 705 up to the wearable device 104-d to perform a synchronization procedure (e.g., first synchronization point) before the PPG data 715-a, 715-b is acquired to determine PTTs 725. In additional or alternative implementations, the user may again be prompted to hold the imaging device 705 up to the wearable device 104-d to perform another (or alternative) synchronization procedure (e.g., second synchronization point) after acquiring the PPG data 715-a, 715-b and determining the PTT 725. In some cases, performing synchronization procedures before and after acquiring the PPG data 715-a, 715-b used to determine the PTT 725 may help ensure that the internal clocks of the respective devices did not drift from one another while the blood pressure spot check was performed.

In cases where multiple synchronization procedures are performed (e.g., before and after collecting PPG data 715, determining pulse observation times 720, and determining PTT(s) 725), the multiple synchronization sessions/procedures may be used to adjust pulse observation times 720 used to calculate PTTs 725. For example, in some cases, a first synchronization procedure (e.g., first synchronization point) may be determined prior to a blood pressure spot check to determine a first delay between internal clocks at the wearable device 104-d and the imaging device 705. Following the first synchronization procedure, a blood pressure spot check may be performed during which the wearable device 104-d and the imaging device 705 collect PPG data 715-a, 715-b associated with multiple heartbeat pulses. Pulse observation times 720 may be determined for each heartbeat pulse. Following the blood pressure spot check, a second calibration procedure (e.g., second synchronization point) may be determined prior to a blood pressure spot check to determine a second delay between internal clocks at the wearable device 104-d and the imaging device 705.

Continuing with this example, the first synchronization procedure (e.g., first synchronization point) and the second synchronization procedure (e.g., second synchronization point) may be used to synchronize internal clocks at the devices, and/or shift/stretch PPG data 715 collected during the blood pressure spot check. In particular, determined pulse observation times 720 (and/or determined PTTs 725) may be selectively adjusted based on the first delay determined based on the first synchronization procedure prior to the blood pressure spot check, and the second delay determined based on the second synchronization procedure following the blood pressure spot check. In particular, pulse observation times 720 collected earlier during the blood pressure spot check may be temporally closer (and more affected by) the first delay determined based on the first synchronization procedure. Conversely, pulse observation times 720 collected later during the blood pressure spot check may be temporally closer (and more affected by) the second delay determined based on the second synchronization procedure. As such, PTTs 725 may be selectively adjusted differently based on the first delay and/or the second delay based on whether the respective PTT 725 is associated with a heartbeat pulse that occurred closer to the first synchronization procedure or the second synchronization procedure.

Stated differently, one synchronization point (e.g., a single synchronization procedure) can be used to remove the bias in time axes of two PPG segments (e.g., PPG data 715-*a*, 715-*b*) collected during the blood pressure spot check (e.g., single synchronization procedure may be used to account for delay between internal clocks of the devices). Two synchronization points (e.g., two synchronization procedures) can also be used to remove drift (different clock rates) from the two PPG segments (e.g., PPG data 715-*a*, 715-*b*). Thus, with two synchronization procedures/points, techniques described herein may enable the two PPG segments (e.g., PPG data 715-*a*, PPG data 715-*b*) acquired during the blood pressure spot check to be aligned more accurately (e.g., delays between devices removed) and resampled, thereby resulting in more accurate measurement of PTTs 725 (and more accurate blood pressure estimates).

For instance, a first subset of pulse observation times 720 associated with heartbeat pulses earlier in time (e.g., closer to the first synchronization procedure) may be selectively adjusted based on the first delay (or based on a weighted average between the first delay and the second delay that more heavily favors the first delay). Conversely, a second subset of pulse observation times 720 associated with heartbeat pulses later in time (e.g., closer to the second synchronization procedure) may be selectively adjusted based on the second delay (or based on a weighted average between the first delay and the second delay that more heavily favors the second delay). In other words, PPG data segments including pulse observation times 720 within the PPG data 715 may be shifted/stretched differently based on the respective delays determined based on synchronization procedures performed before/after the blood pressure spot check. Subsequently, the adjusted PPG data may be resampled, and shifted/aligned pulse observation times 720 may be used to calculate PTTs 725, which are used to determine/estimate a blood pressure metric (and/or other physiological metric) of the user.

While the synchronization procedures described herein are described as being used to synchronize internal clocks and/or collected PPG segments between the imaging device 705 and the wearable device 104-*d*, this is not to be regarded as a limitation of the present disclosure, unless noted otherwise herein. In particular, the synchronization procedures described herein may be used to synchronize any types of devices, such as syncing clocks/data between (1) the wearable device 104-*d* and the user device 106-*b*, (2) the wearable device 104-*d* and the imaging device 705, (3) between multiple wearable devices 104 (such as in cases where the imaging device 705 is included within another wearable device 104), and the like. Further, in some cases, the imaging device 705 may be configured to perform synchronization procedures with multiple wearable devices 104 (e.g., multiple rings), where the separate synchronization procedures may be used to synchronize/calibrate the multiple wearable devices 104 themselves. For instance, the imaging device 705 may perform a first synchronization procedure with a first wearable device 104-*d* to determine a first delay between clocks at the imaging device 705 and the first wearable device 104-*d*. Similarly, the imaging device

705 may perform a second synchronization procedure with a second wearable device 104 to determine a second delay between clocks at the imaging device 705 and the second wearable device 104. In this example, the synchronization procedures may be used to synchronize/calibrate the imaging device 705 with the respective wearable devices 104, and also synchronize/calibrate the internal clocks between the respective wearable devices 104.

As described previously herein, blood pressure spot checks may additionally or alternatively be performed using a microphone or other audio component of the wearable device 104-*b*. That is, instead of using the imaging device 705 that collects images to determine pulse observation times 720, a blood pressure spot check may be performed by using a microphone of the user device 106-*b* that collects audio data that is used to determine pulse observation times 720. For instance, the user may hold the user device 106-*b* up to their chest such that a microphone of the user device 106-*b* can collect sound data that is used to determine when the user's heart beats. In this regard, sound data collected from the microphone of the user device 106-*b* may be used to determine a first pulse observation time 720-*a*, where the wearable ring device 104-*b* may be used to determine a second pulse observation time 720-*b*. As described previously herein, the respective pulse observation times 720-*a*, 720-*b* may be used to determine a PTT 725 and/or other physiological metrics, such as PWV, blood pressure, arterial stiffness, arterial plaque, cardiovascular age metrics, and the like.

In cases where audio data is used to determine pulse observation times 720, one or more algorithms, machine learning models, or other mathematical formulas may be used to determine pulse observation times 720 from the audio data. In some cases, such algorithms/models may identify peaks within the audio data that correspond to heartbeats. As such, the system 700 may utilize one or more peak-finding algorithms to analyze sound data, identify peaks within the sound data, and determine pulse observation times 720 of heartbeats corresponding to identified peaks.

In the context of sound-based spot checks, synchronization procedures may be performed in order to synchronize/coordinate audio data collected via a microphone (e.g., audio component) of the user device 106 and data collected by the wearable ring device 105-*d*. For example, after initiating a blood pressure spot check, the user may be instructed to perform a synchronization procedure by "knocking" or "tapping" the wearable ring device 104-*d* against the user device 106-*b*. During the synchronization procedure, acceleration/motion data collected by the wearable ring device 104-*b* may be used to determine when the knocks/taps are observed by the wearable ring device 104-*d*. Similarly, audio data collected by the microphone of the user device 106-*b* may be used to determine when the knocks/taps are observed by the user device 106-*b*.

As such, the acceleration data from the ring and the audio data from the user device 106-*b* may be used to identify delays between internal clocks of the respective devices, as described previously herein. Subsequently, during an audio-based spot check, the user may hold the user device 106-*b* up to their chest to collect audio data, where the wearable ring device 104-*d* may collect PPG and/or acceleration data at the user's finger, where pulse observation times 720 may be identified from the audio data and the PPG data. Identified delays between internal clocks at the user device 106-*b* and the wearable ring device 104-*b* may then be used to synchronize or otherwise coordinate (e.g., align) the audio data collected by the microphone of the user device 106-*b* and the PPG data (and/or acceleration data) collected by the wearable ring device 104-*b*, as described previously herein (such as by "shifting" the audio data or the PPG data by the identified delay(s)).

Figure 8:
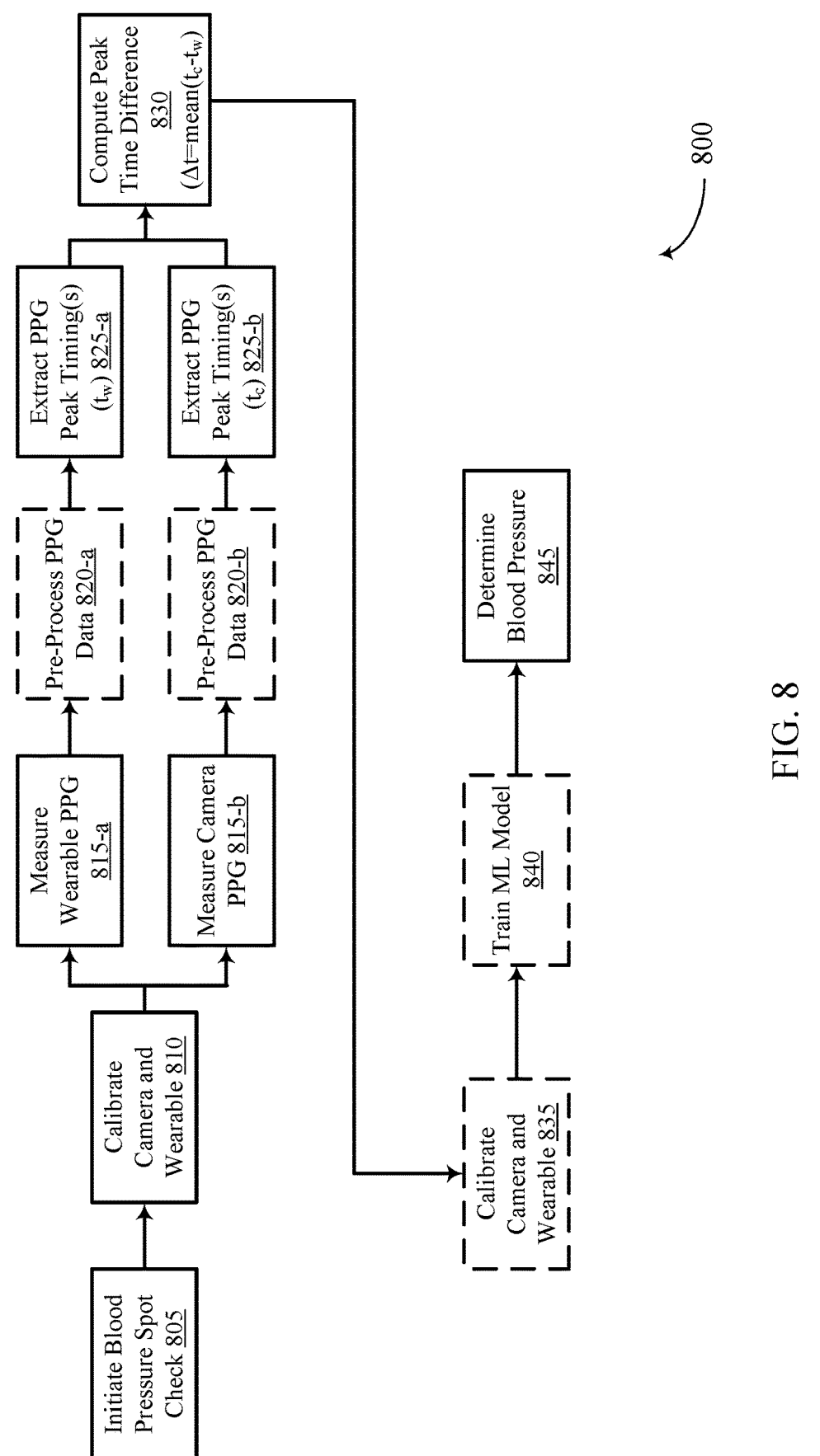
FIG. 8 shows an example of a flow diagram that supports techniques for determining blood pressure based on a relative timing of pulses in accordance with aspects of the present disclosure.

FIG. 8 illustrates a flow diagram 800 that supports techniques for determining blood pressure based on a relative timing of pulses in accordance with aspects of the present disclosure. Aspects of the flow diagram 800 may implement, or be implemented by, aspects of the system 100, the system 200, the system 300, the system 400, the timing diagram 500, the GUI 600, the system 700, or any combination thereof. In particular, the flow diagram 800 illustrates an example blood pressure spot check used to estimate a user's blood pressure, as described previously herein. At 805, a user may initiate a blood pressure spot check. For example, the user may input a command via a GUI of the user device 106-*b* to initiate a blood pressure spot check.

At 810, the system may perform a synchronization procedure to identify a delay between internal clocks at the wearable device 104-*d* and the imaging device 705. In some cases, the GUI of the user device 106 may display instructions that instruct the user to perform the synchronization procedure. As described previously herein, the instructions may instruct the user to hold the imaging device 705 up to the wearable device 104-*d*, where the wearable device 104-*d* may flash LEDs and the imaging device 705 takes images (e.g., a video stream) of the flashing LEDs.

In this regard, at 810, the system 700 (e.g., processors of the wearable device 104-*d*, user device 106-*b*, imaging device 705, servers 110, or any combination thereof) may be configured to perform a synchronization procedure to identify a delay between internal clocks at the wearable device 104-*d* and the imaging device 705 based on the images of the flashing LEDs captured by the imaging device 705. In particular, the synchronization procedure may be performed to determine when the LEDs were flashed by the wearable device 104-*d*, and when the flashing LEDs were observed by the imaging device 705.

Additionally, or alternatively, in the context of audio-based spot checks, the instructions may instruct the user to "knock" or "tap" the wearable ring device 104-*d* against the user device 106-*b*. In this example, the system 700 may perform a synchronization procedure to identify a delay between internal clocks at the wearable device 104-*d* and the microphone of the user device 106-*b* based on acceleration data captured by the wearable ring device 104-*d* (e.g., acceleration data to identify the knocks/taps), and audio data collected by the microphone (e.g., audio data to identify the knocks/taps). The acceleration data and the audio data may then be used to identify a delay between internal clocks at the wearable device 104-*d* and the microphone (e.g., user device 106-*b*).

The delay between the internal clocks at the respective devices, as determined by the synchronization procedure, may then be used to synchronize the internal clocks of the respective devices and/or to adjust determined pulse observation times 720 that are used to determine PTTs 725 and estimate blood pressure metrics (and/or other physiological parameters).

For example, the system 700 may be configured to determine a delay between a first time that the LEDs of the wearable device 104-*d* were flashed, and a second time that the flashing of the LEDs were observed by the imaging device 705 based on the images captured by the imaging device 705. For instance, the system 700 may receive/determine a first timestamp indicating a first time that the LEDs were flashed, and may receive/determine a second timestamp indicating a second time that the flashing LEDs were observed by the imaging device 705. In this example, the system 700 may determine a delay between a first internal clock at the wearable device 104-*d* and a second internal clock at the imaging device 705 based on the received/determined timestamps.

By way of another example, the system 700 may be configured to determine a delay between a first time that the microphone of the user device 106-*b* observed the knocks/taps, and a second time that the motion sensors (e.g., acceleration sensors, gyroscopes) of the wearable device 104-*d* observed the knocks/taps. For instance, the system 700 may receive/determine a first timestamp indicating a first time that the knocks/taps were observed via the audio data collected by the microphone, and may receive/determine a second timestamp indicating a second time that the knocks/taps were observed via the acceleration data collected by the wearable device 104-*d*. In this example, the system 700 may determine a delay between a first internal clock at the user device 106-*b* and a second internal clock at the wearable device 104-*d* based on the received/determined timestamps.

In accordance with a first implementation, the determined delay may be used to synchronize internal clocks/clock rates at the respective devices. Subsequently, after synchronizing internal clocks at the respective devices, the wearable device 104-*d* and the imaging device 705 may collect the PPG data 715-*a*, 715-*b*, and the system 700 may determine pulse observation times 720 within the synchronized PPG data streams, and determine PTTs 725 that are used to estimate blood pressure metrics (and/or other physiological parameters).

In accordance with a second implementation, the delay determined via the synchronization procedure may be used to shift/stretch PPG data 715 collected during the blood pressure spot check, while enabling the wearable device 104-*b* and the imaging device 705 to maintain separate (e.g., unsynchronized) internal clocks. For example, following the synchronization procedure, the wearable device 104-*d* and the imaging device 705 may collect the PPG data 715-*a*, 715-*b*, and the determined delay may then be used to adjust determined pulse observation times 720 within the PPG data 715 collected during the blood pressure spot check (and without otherwise fully synchronizing the internal clocks at the respective devices). Subsequently, the shifted/aligned PPG data (e.g., shifted pulse observation times 720) may be used to estimate blood pressure metrics (and/or other physiological parameters). For instance, the second pulse observation time 720-*b* observed by the imaging device 705 may be shifted up by the determined delay, and the PTT 725 may be calculated based on the shifted second pulse observation time 720-*b*. The second implementation may result in different segments of PPG data 715 collected by the wearable device 104-*b* and the imaging device 705 being aligned or misaligned, where PPG data 715 that is shifted according to the delay is aligned/synchronized, and where PPG data 715 that is not shifted is not aligned/synchronized.

At 815-*a*, the wearable device 104-*d* may acquire physiological data (e.g., PPG data 715-*a*) from the user at a first physiological location (e.g., at the base of the finger). Similarly, at 815-*b*, the imaging device 705 may acquire physiological data (e.g., PPG data 715-*b*) from the user at a second physiological location (e.g., at the fingertip). Alternatively, in the context of an audio-based spot check, at 815-*b*, the user may hold the microphone of the user device 106-*b* up to their chest so that the microphone can collect audio data that may be used to identify when the user's heart beats.

At 820-*a* and 820-*b*, the physiological data (e.g., PPG data 715-*a*, 715-*b*, and/or audio data indicative of heartbeats) acquired by the wearable device 104-*d* and the imaging device 705 may be pre-processed. During pre-processing, one or more processors may perform filtering and resampling operations and/or other mathematical operations/algorithms on the PPG data 715-*a*, 715-*b* collected at 815-*a* and 815-*b*.

At 825-*a*, the system 700 may extract peak timings ($t_w$) of heartbeat pulses within the PPG data 715-*a* collected via the wearable device 104-*d* at 815-*a*. That is, the system 700 may determine pulse observation times 720-*a* ($t_w$) of heartbeat pulses within the PPG data 715-*a*. Similarly, at 825-*b*, the system 700 may extract peak timings ($t_c$) of heartbeat pulses within the PPG data 715-*b* collected via the imaging device 705 at 815-*b*. That is, the system 700 may determine pulse observation times 720-*b* ($t_c$) of heartbeat pulses within the PPG data 715-*b*. Moreover, in the context of an audio-based spot check, at 825-*b*, the system 700 may extract peak timings ($t_c$) of heartbeat pulses within audio data collected via the microphone of the user device 106-*b* in order to identify pulse observation times 720-*b* of heartbeat pulses within the audio data.

At 830, the system may perform an additional (or alternative) synchronization procedure to identify a delay (e.g., additional delay) between internal clocks at the wearable device 104-*d* and the imaging device 705 (and/or microphone/audio device), as described in step 810. As such, any description associated with the synchronization procedure in step 810 may also be understood to apply to the synchronization procedure at step 830.

As noted previously herein, the first synchronization procedure at 810 and/or the second synchronization procedure at 830 may be used to determine delays/differences between internal clocks at the wearable device 104-*d* and the imaging device 705 (and/or microphone), where the differences/delays (bias and drift) may be used to (1) synchronize/align internal clocks at the respective devices, and/or (2) shift/stretch/align PPG segments collected during the blood pressure spot check (e.g., selectively adjust pulse observation times 720 determined at 825-*a* and 825-*b*).

At 835, the system 700 may compute peak time differences (e.g., PTTs 725) between the peak timings (e.g., pulse observation times 720 ($t_w$, $t_c$)) determined at 825-*a* and 825-*b*. As described previously herein, the peak time difference, or PTT 725, may be calculated as the average time difference between pulse observation times 720 for each respective heartbeat (e.g., $PTT=\Delta t=mean(t_{w,i}-t_{c,i})$). Moreover, the system 700 may calculate the PTTs 725 at 835 based on performing the synchronization procedure(s) at 810 and/or 830. In this regard, calculation of the PTTs 725 may be performed by (1) synchronizing internal clocks at the respective devices based on determined delay(s), and/or (2) shifting/stretching, or otherwise aligning, PPG segments collected during the blood pressure spot check by the determined delay(s).

In some aspects, the PTTs 725 may be determined based on (1) determining a mean of segment peak timing differences (e.g., average PTT across multiple heartbeat pulses), and/or (2) a cross-correlation of the full PPG data 715-*a*, 715-*b* segments. In the context of cross correlation, the system 700 may identify a first set of peaks indicating heartbeat pulses within the PPG data 715-*a* collected via the wearable device 104-*d*, and a second set of peaks indicating heartbeat pulses within the PPG data 715-*b* collected via the imaging device 705. Subsequently, the system 700 may manipulate (e.g., shift, stretch) the PPG data 715-*b* collected by the imaging device 705 to align the second set of peaks within the PPG data 715-*b* with the first set of peaks with the PPG data 715-*a*. The distance that the PPG data 715-*b* data is moved to align the peaks may be determined as the PTT 725 for the segment of PPG data 715-*a*, 715-*b*.

At 840, the system 700 may train one or more machine learning models to determine blood pressure metrics (and/or other physiological metrics, such as PWV, arterial stiffness, arterial plaque, cardiovascular age metrics, etc.) for the user based on determined PTTs 725. As described previously herein, the relationship between PTTs 725 and blood pressure metrics may be based on the distance (d) between physiological locations that the respective pulse observation times 720 were determined. As such, in some cases, separate machine learning models may be trained based on where the blood pressure spot check is being performed. For example, a first machine learning model may be trained to determine blood pressure metrics when the blood pressure spot check is performed on the user's index finger (e.g., first distance $d_1$), and a second machine learning model may be trained to determine blood pressure metrics when the blood pressure spot check is performed on the user's ring finger (e.g., second distance $d_2$).

In additional or alternative cases, a single machine learning model may be used to calculate blood pressure metrics using PTTs 725 on different fingers by utilizing different distance (d) metrics for the respective fingers. In some aspects, the one or more machine learning models may be configured to utilize multiple parameters or variables to calculate blood pressure based on PTT 725, including distance values (d), an age of the user, sex of the user, BMI of the user, the user's baseline blood pressure values, previous diagnosis of hypertension, and the like.

In order to train the machine learning model(s), an external device (such as a blood pressure cuff) may be used to determine blood pressure metrics for the user over a time interval. During the same time interval, the wearable device 104-*d* and the imaging device 705 may be used to collect PPG data 715 and determine PTTs 725 of heartbeat pulses within the time interval. In this example, the blood pressure metrics from the blood pressure cuff and the PTTs 725 determined from the blood pressure spot check may be input into the machine learning model. In this regard, the machine learning model may be trained to determine blood pressure metrics for the user (and for the specific physiological locations blood pressure spot check was performed) based on determined PTTs 725.

At 845, the system 700 may determine one or more blood pressure metrics for the user. The system 700 may determine the blood pressure metrics based on performing the first synchronization procedure at 810, measuring the PPG data 715 at 815-*a* and 815-*b*, pre-processing the PPG data at 820-*a* and 820-*b*, determining pulse observation times 720 at 825-*a* and 825-*b*, performing the second synchronization procedure at 830, adjusting PPG data/pulse observation times 720 based on determined delays between internal clocks at the wearable device 104-*d* and imaging device 705 (and/or synchronizing internal clocks at the respective devices), determining PTTs 725 at 835, training the machine learning model at 840, or any combination thereof.

Figure 9:
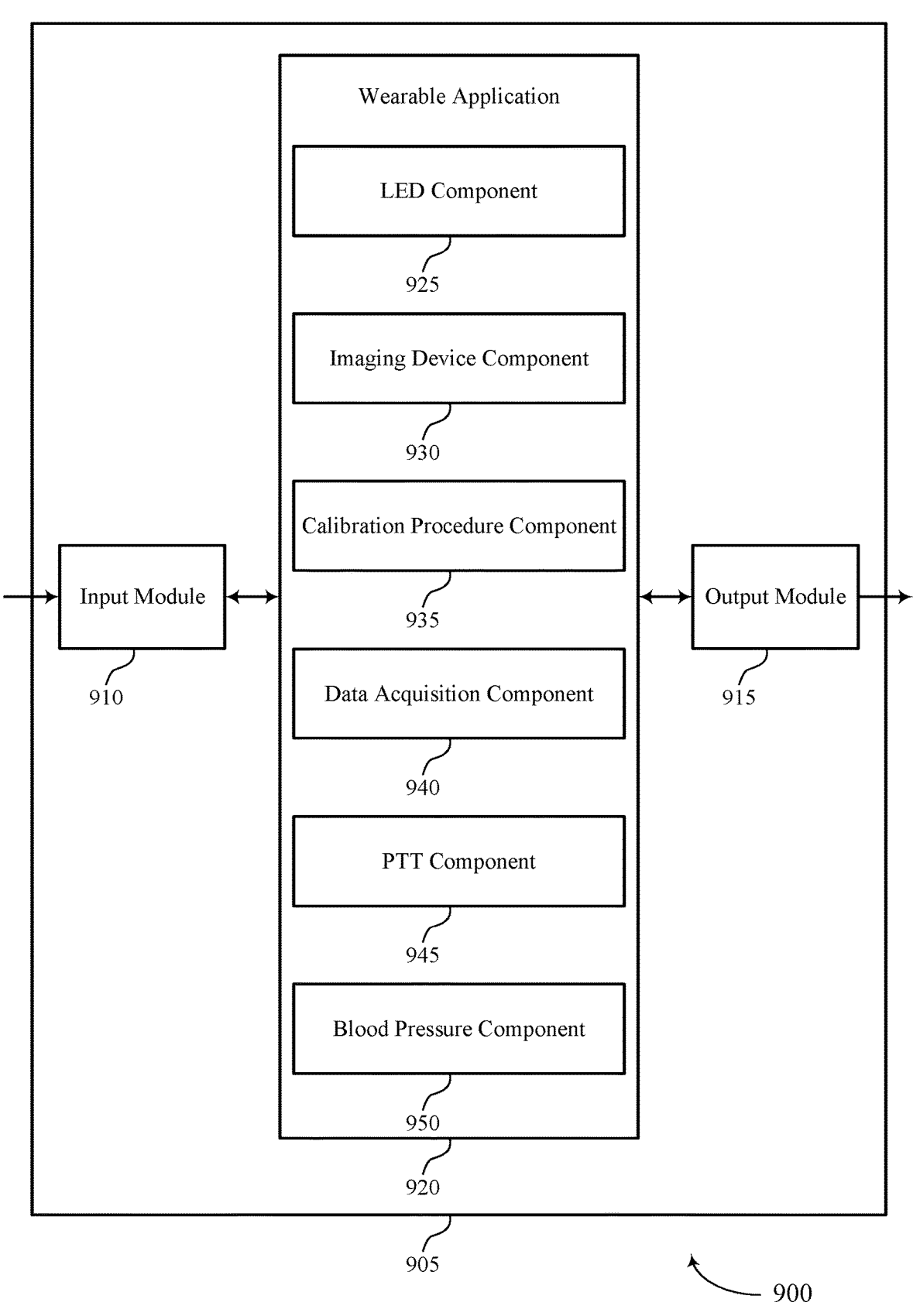
FIG. 9 shows a block diagram of an apparatus that supports techniques for determining blood pressure based on a relative timing of pulses in accordance with aspects of the present disclosure.

FIG. 9 shows a block diagram 900 of a device 905 that supports techniques for determining blood pressure based on a relative timing of pulses in accordance with aspects of the present disclosure. The device 905 may include an input module 910, an output module 915, and a wearable application 920. The device 905, or one or more components of the device 905 (e.g., the input module 910, the output module 915, and the wearable application 920), may include at least one processor, which may be coupled with at least one memory, to support the described techniques. Each of these components may be in communication with one another (e.g., via one or more buses).

The input module 910 may provide a means for receiving information such as packets, user data, control information, or any combination thereof associated with various information channels (e.g., control channels, data channels, information channels related to illness detection techniques). Information may be passed on to other components of the device 905. The input module 910 may utilize a single antenna or a set of multiple antennas.

The output module 915 may provide a means for transmitting signals generated by other components of the device 905. For example, the output module 915 may transmit information such as packets, user data, control information, or any combination thereof associated with various information channels (e.g., control channels, data channels, information channels related to illness detection techniques). In some examples, the output module 915 may be co-located with the input module 910 in a transceiver module. The output module 915 may utilize a single antenna or a set of multiple antennas.

For example, the wearable application 920 may include a LED component 925, an imaging device component 930, a synchronization procedure component 935, a data acquisition component 940, a PTT component 945, a blood pressure component 950, or any combination thereof. In some examples, the wearable application 920, or various components thereof, may be configured to perform various operations (e.g., receiving, monitoring, transmitting) using or otherwise in cooperation with the input module 910, the output module 915, or both. For example, the wearable application 920 may receive information from the input module 910, send information to the output module 915, or be integrated in combination with the input module 910, the output module 915, or both to receive information, transmit information, or perform various other operations as described herein.

The LED component 925 may be configured as or otherwise support a means for flashing one or more light-emitting components of a wearable device, the wearable device configured to acquire physiological data from a user. The imaging device component 930 may be configured as or otherwise support a means for capturing one or more images of the flashing one or more light-emitting components using an imaging device. The synchronization procedure component 935 may be configured as or otherwise support a means for performing a synchronization procedure between a first internal clock of the wearable device and a second internal clock of the imaging device based at least in part on capturing the one or more images. The data acquisition component 940 may be configured as or otherwise support a means for acquiring first physiological data at a first physiological location of a body of the user via the wearable device, the first physiological data indicating a first pulse observation time of a heartbeat of the user at the first physiological location. The data acquisition component 940 may be configured as or otherwise support a means for acquiring second physiological data at a second physiological location of the body of the user via the imaging device, the second physiological data indicating a second pulse observation time of the heartbeat, an additional heartbeat of the user, or both, at the second physiological location. The PTT component 945 may be configured as or otherwise support a means for determining, based at least in part on the synchronization procedure, a PTT associated with the heartbeat, the additional heartbeat, or both, based at least in part on a comparison between the first pulse observation time and the second pulse observation time. The blood pressure component 950 may be configured as or otherwise support a means for determining a blood pressure metric for the user based at least in part on the PTT.

Figure 10:
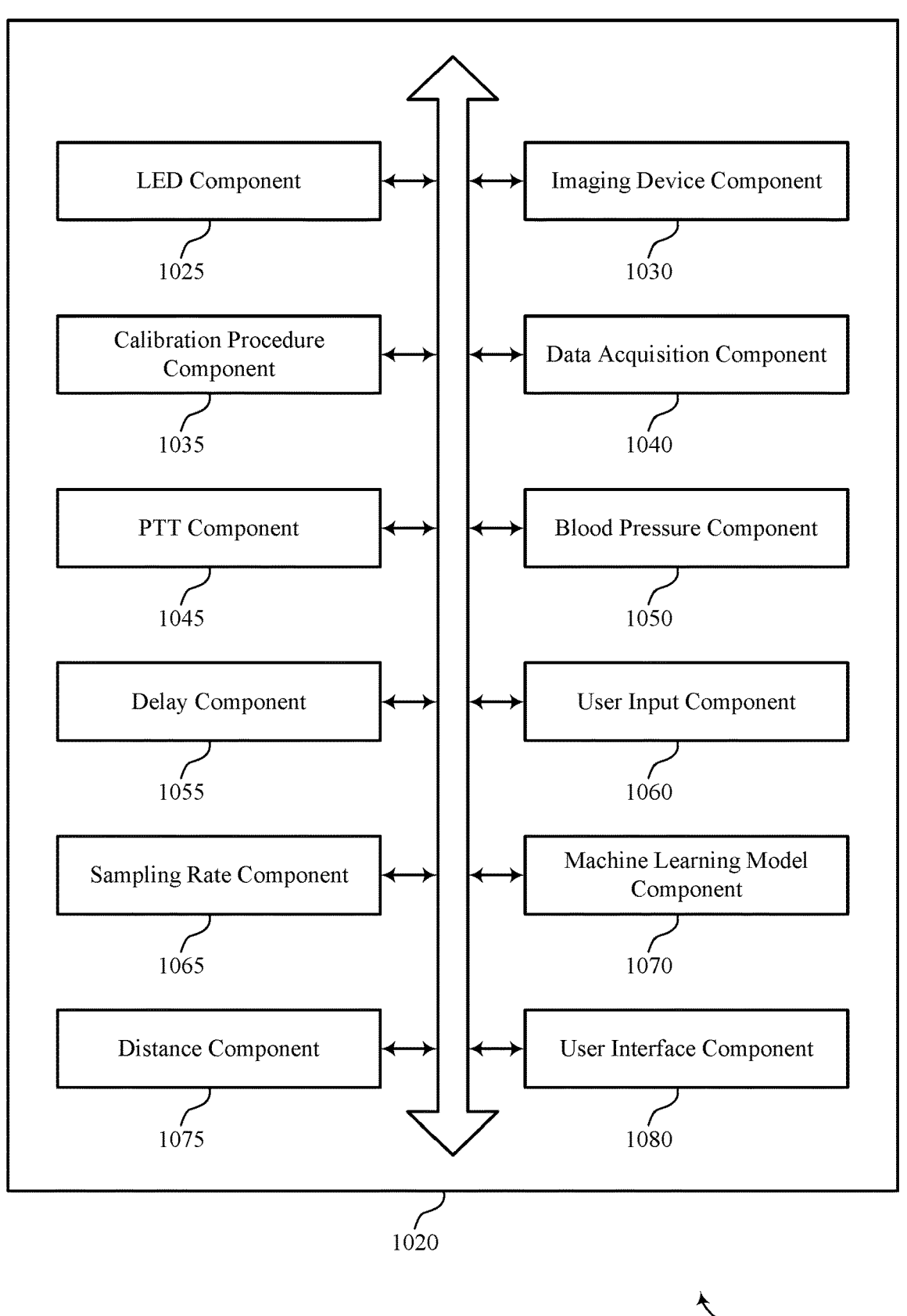
FIG. 10 shows a block diagram of a wearable application that supports techniques for determining blood pressure based on a relative timing of pulses in accordance with aspects of the present disclosure.

FIG. 10 shows a block diagram 1000 of a wearable application 1020 that supports techniques for determining blood pressure based on a relative timing of pulses in accordance with aspects of the present disclosure. The wearable application 1020 may be an example of aspects of a wearable application or a wearable application 920, or both, as described herein. The wearable application 1020, or various components thereof, may be an example of means for performing various aspects of techniques for determining blood pressure based on a relative timing of pulses as described herein. For example, the wearable application 1020 may include a LED component 1025, an imaging device component 1030, a synchronization procedure component 1035, a data acquisition component 1040, a PTT component 1045, a blood pressure component 1050, a delay component 1055, a user input component 1060, a sampling rate component 1065, a machine learning model component 1070, a distance component 1075, a user interface component 1080, or any combination thereof. Each of these components, or components of subcomponents thereof (e.g., one or more processors, one or more memories), may communicate, directly or indirectly, with one another (e.g., via one or more buses).

The LED component 1025 may be configured as or otherwise support a means for flashing one or more light-emitting components of a wearable device, the wearable device configured to acquire physiological data from a user. The imaging device component 1030 may be configured as or otherwise support a means for capturing one or more images of the flashing one or more light-emitting components using an imaging device. The synchronization procedure component 1035 may be configured as or otherwise support a means for performing a synchronization procedure between a first internal clock of the wearable device and a second internal clock of the imaging device based at least in part on capturing the one or more images. The data acquisition component 1040 may be configured as or otherwise support a means for acquiring first physiological data at a first physiological location of a body of the user via the wearable device, the first physiological data indicating a first pulse observation time of a heartbeat of the user at the first physiological location. In some examples, the data acquisition component 1040 may be configured as or otherwise support a means for acquiring second physiological data at a second physiological location of the body of the user via the imaging device, the second physiological data indicating a second pulse observation time of the heartbeat, an additional heartbeat of the user, or both, at the second physiological location. The PTT component 1045 may be configured as or otherwise support a means for determining, based at least in part on the calibration procedure, a PTT associated with the heartbeat, the additional heartbeat, or both, based at least in part on a comparison between the first pulse observation time and the second pulse observation time. The blood pressure component 1050 may be configured as or otherwise support a means for determining a blood pressure metric for the user based at least in part on the PTT.

In some examples, to support performing the synchronization procedure, the delay component 1055 may be configured as or otherwise support a means for determining a delay between when the one or more light-emitting components of the wearable device were flashed and when the flashing of the one or more light-emitting components was observed by the imaging device based at least in part on capturing the one or more images. In some examples, to support performing the synchronization procedure, the PTT component 1045 may be configured as or otherwise support a means for selectively adjusting the PTT based at least in part on the delay, wherein determining the blood pressure metric is based at least in part on selectively adjusting the PTT.

In some examples, to support determining the delay, the delay component 1055 may be configured as or otherwise support a means for receiving, from the wearable device, at least a first timestamp indicating a first time that the one or more light-emitting components were flashed. In some examples, to support determining the delay, the delay component 1055 may be configured as or otherwise support a means for determining a second timestamp indicating a second time that the flashing of the one or more light-emitting components was observed by the imaging device based at least in part on capturing the one or more images, wherein the delay is based at least in part on the first timestamp and the second timestamp.

In some examples, the user input component 1060 may be configured as or otherwise support a means for receiving, via a user device communicatively coupled with the wearable device, a user input that initiates a blood pressure spot check procedure, wherein flashing the one or more light-emitting components, capturing the one or more images, performing the synchronization procedure, acquiring the first physiological data, acquiring the second physiological data, or any combination thereof, is based at least in part on receiving the user input.

In some examples, the user interface component 1080 may be configured as or otherwise support a means for displaying, via a graphical user interface (GUI) of the user device and in response to the user input, a set of instructions for performing the synchronization procedure, wherein the set of instructions indicate for the user to capture the one or more images of the flashing one or more light-emitting components.

In some examples, the first physiological data is acquired by the wearable device using the one or more light-emitting components at a first power level. In some examples, flashing the one or more light-emitting components comprises flashing the one or more light-emitting components at a second power level that is greater than the first power level.

In some examples, the sampling rate component 1065 may be configured as or otherwise support a means for synchronizing a first sampling rate associated with the one or more light-emitting components and a second sampling rate associated with the imaging device based at least in part on performing the synchronization procedure, wherein the first physiological data is acquired by the wearable device in accordance with the first sampling rate based at least in part on the synchronizing, and wherein the second physiological data is acquired by the imaging device in accordance with the second sampling rate based at least in part on the synchronizing.

In some examples, the LED component 1025 may be configured as or otherwise support a means for flashing, during a second time interval subsequent to the first time interval, the one or more light-emitting components of the wearable device. In some examples, the imaging device component 1030 may be configured as or otherwise support a means for capturing one or more additional images of the flashing one or more light-emitting components using the imaging device during the second time interval. In some examples, the synchronization procedure component 1035 may be configured as or otherwise support a means for performing a second synchronization procedure between the first internal clock of the wearable device and the second internal clock of the imaging device based at least in part on capturing the one or more additional images, wherein determining the PTT is based at least in part on the synchronization procedure and the second synchronization procedure.

In some examples, the blood pressure component 1050 may be configured as or otherwise support a means for receiving one or more blood pressure metrics associated with a user that are measured from an external device throughout a time interval. In some examples, the PTT component 1045 may be configured as or otherwise support a means for determining one or more PTTs associated with the user based at least in part on third physiological data acquired by the wearable device at the first physiological location throughout the time interval, and fourth physiological data acquired by the imaging device at the second physiological location throughout the time interval. In some examples, the machine learning model component 1070 may be configured as or otherwise support a means for training a machine learning model to determine blood pressure metrics for the user based on PTTs observed between the first physiological location and the second physiological location based at least in part on inputting the one or more PTTs and the one or more blood pressure metrics into the machine learning model, wherein the blood pressure metric is determined by the machine learning model based at least in part on training the machine learning model.

In some examples, the distance component 1075 may be configured as or otherwise support a means for receiving an indication of a distance between the first physiological location and the second physiological location, wherein determining the blood pressure metric is based at least in part on the PTT and the distance.

In some examples, the imaging device component 1030 may be configured as or otherwise support a means for receiving, from the imaging device, one or more additional images of the body of the user between the first physiological location and the second physiological location. In some examples, the distance component 1075 may be configured as or otherwise support a means for determining the distance between the first physiological location and the second physiological location based at least in part on the one or more additional images.

In some examples, the first physiological location comprises a first location at a base of a finger of the user. In some examples, the second physiological location comprises a second location at a tip of the finger of the user.

In some examples, the imaging device comprises a second wearable device configured to acquire physiological data from the user.

In some examples, the wearable device comprises a wearable ring device.

Figure 11:
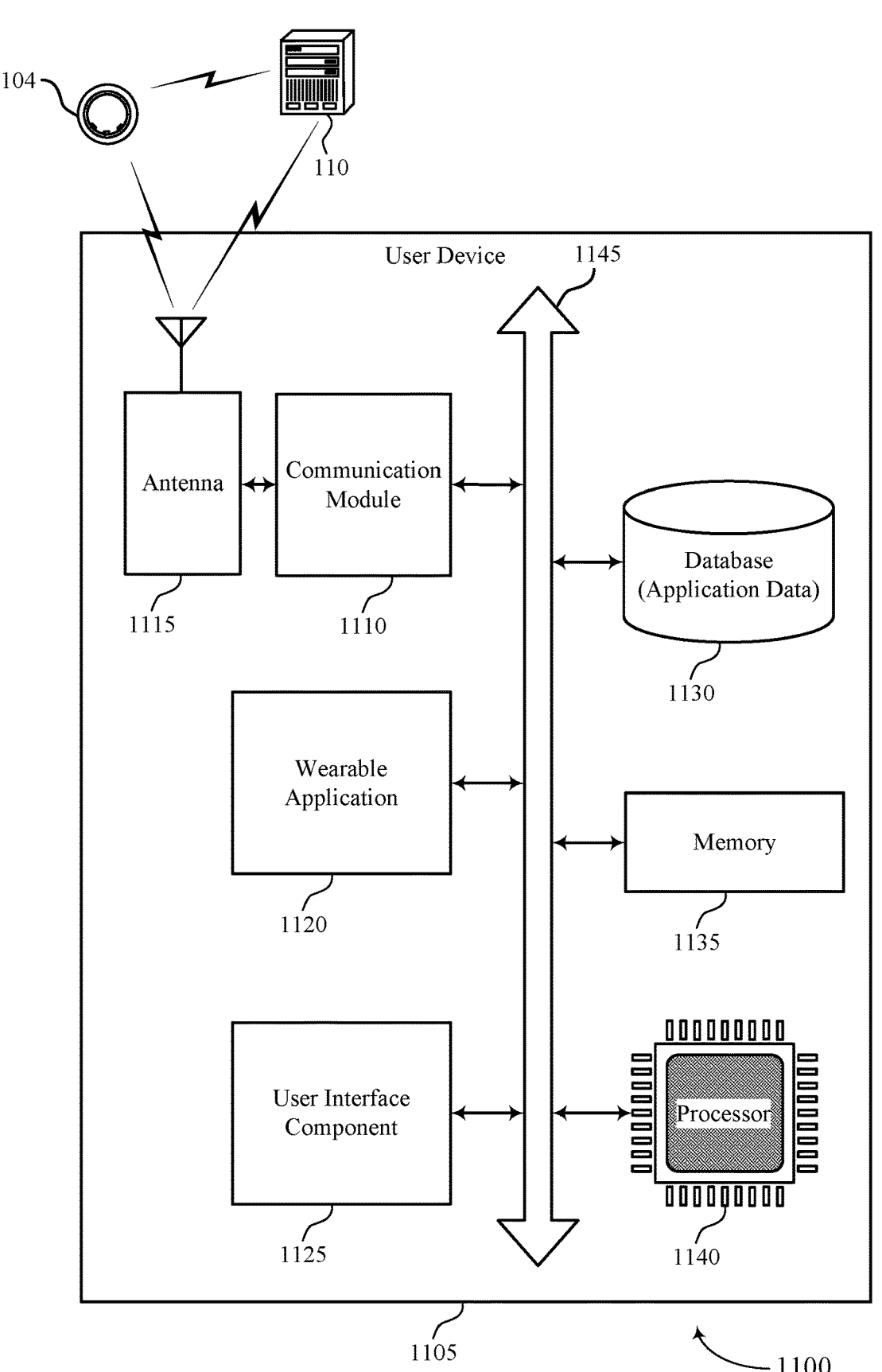
FIG. 11 shows a diagram of a system including a device that supports techniques for determining blood pressure based on a relative timing of pulses in accordance with aspects of the present disclosure.

FIG. 11 shows a diagram of a system 1100 including a device 1105 that supports techniques for determining blood pressure based on a relative timing of pulses in accordance with aspects of the present disclosure. The device 1105 may be an example of or include the components of a device 905 as described herein. The device 1105 may include an example of a user device 106, as described previously herein. The device 1105 may include components for bi-directional communications including components for transmitting and receiving communications with a wearable device 104 and a server 110, such as a wearable application 1120, a communication module 1110, an antenna 1115, a user interface component 1125, a database (application data) 1130, at least one memory 1135, and at least one processor 1140. These components may be in electronic communication or otherwise coupled (e.g., operatively, communicatively, functionally, electronically, electrically) via one or more buses (e.g., a bus 1145).

The communication module 1110 may manage input and output signals for the device 1105 via the antenna 1115. The communication module 1110 may include an example of the communication module 220-b of the user device 106 shown and described in FIG. 2. In this regard, the communication module 1110 may manage communications with the ring 104 and the server 110, as illustrated in FIG. 2. The communication module 1110 may also manage peripherals not integrated into the device 1105. In some cases, the communication module 1110 may represent a physical connection or port to an external peripheral. In some cases, the communication module 1110 may utilize an operating system such as iOS®, ANDROID®, MS-DOS®, MS-WINDOWS®, OS/2®, UNIX®, LINUX®, or another known operating system. In other cases, the communication module 1110 may represent or interact with a wearable device (e.g., ring 104), modem, a keyboard, a mouse, a touchscreen, or a similar device. In some cases, the communication module 1110 may be implemented as part of the processor 1140. In some examples, a user may interact with the device 1105 via the communication module 1110, user interface component 1125, or via hardware components controlled by the communication module 1110.

In some cases, the device 1105 may include a single antenna 1115. However, in some other cases, the device 1105 may have more than one antenna 1115, which may be capable of concurrently transmitting or receiving multiple wireless transmissions. The communication module 1110 may communicate bi-directionally, via the one or more antennas 1115, wired, or wireless links as described herein. For example, the communication module 1110 may represent a wireless transceiver and may communicate bi-directionally with another wireless transceiver. The communication module 1110 may also include a modem to modulate the packets, to provide the modulated packets to one or more antennas 1115 for transmission, and to demodulate packets received from the one or more antennas 1115.

The user interface component 1125 may manage data storage and processing in a database 1130. In some cases, a user may interact with the user interface component 1125. In other cases, the user interface component 1125 may operate automatically without user interaction. The database 1130 may be an example of a single database, a distributed database, multiple distributed databases, a data store, a data lake, or an emergency backup database.

The memory 1135 may include RAM and ROM. The memory 1135 may store computer-readable, computer-executable software including instructions that, when executed, cause the processor 1140 to perform various functions described herein. In some cases, the memory 1135 may contain, among other things, a BIOS which may control basic hardware or software operation such as the interaction with peripheral components or devices.

The processor 1140 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 1140 may be configured to operate a memory array using a memory controller. In other cases, a memory controller may be integrated into the processor 1140. The processor 1140 may be configured to execute computer-readable instructions stored in a memory 1135 to perform various functions (e.g., functions or tasks supporting a method and system for sleep staging algorithms).

For example, the wearable application 1120 may be configured as or otherwise support a means for flashing one or more light-emitting components of a wearable device, the wearable device configured to acquire physiological data from a user. The wearable application 1120 may be configured as or otherwise support a means for capturing one or more images of the flashing one or more light-emitting components using an imaging device. The wearable application 1120 may be configured as or otherwise support a means for performing a synchronization procedure between a first internal clock of the wearable device and a second internal clock of the imaging device based at least in part on capturing the one or more images. The wearable application 1120 may be configured as or otherwise support a means for acquiring first physiological data at a first physiological location of a body of the user via the wearable device, the first physiological data indicating a first pulse observation time of a heartbeat of the user at the first physiological location. The wearable application 1120 may be configured as or otherwise support a means for acquiring second physiological data at a second physiological location of the body of the user via the imaging device, the second physiological data indicating a second pulse observation time of the heartbeat, an additional heartbeat of the user, or both, at the second physiological location. The wearable application 1120 may be configured as or otherwise support a means for determining, based at least in part on the synchronization procedure, a PTT associated with the heartbeat, the additional heartbeat, or both, based at least in part on a comparison between the first pulse observation time and the second pulse observation time. The wearable application 1120 may be configured as or otherwise support a means for determining a blood pressure metric for the user based at least in part on the PTT.

The wearable application 1120 may include an application (e.g., "app"), program, software, or other component which is configured to facilitate communications with a ring 104, server 110, other user devices 106, and the like. For example, the wearable application 1120 may include an application executable on a user device 106 which is configured to receive data (e.g., physiological data) from a ring 104, perform processing operations on the received data, transmit and receive data with the servers 110, and cause presentation of data to a user 102.

Figure 12:
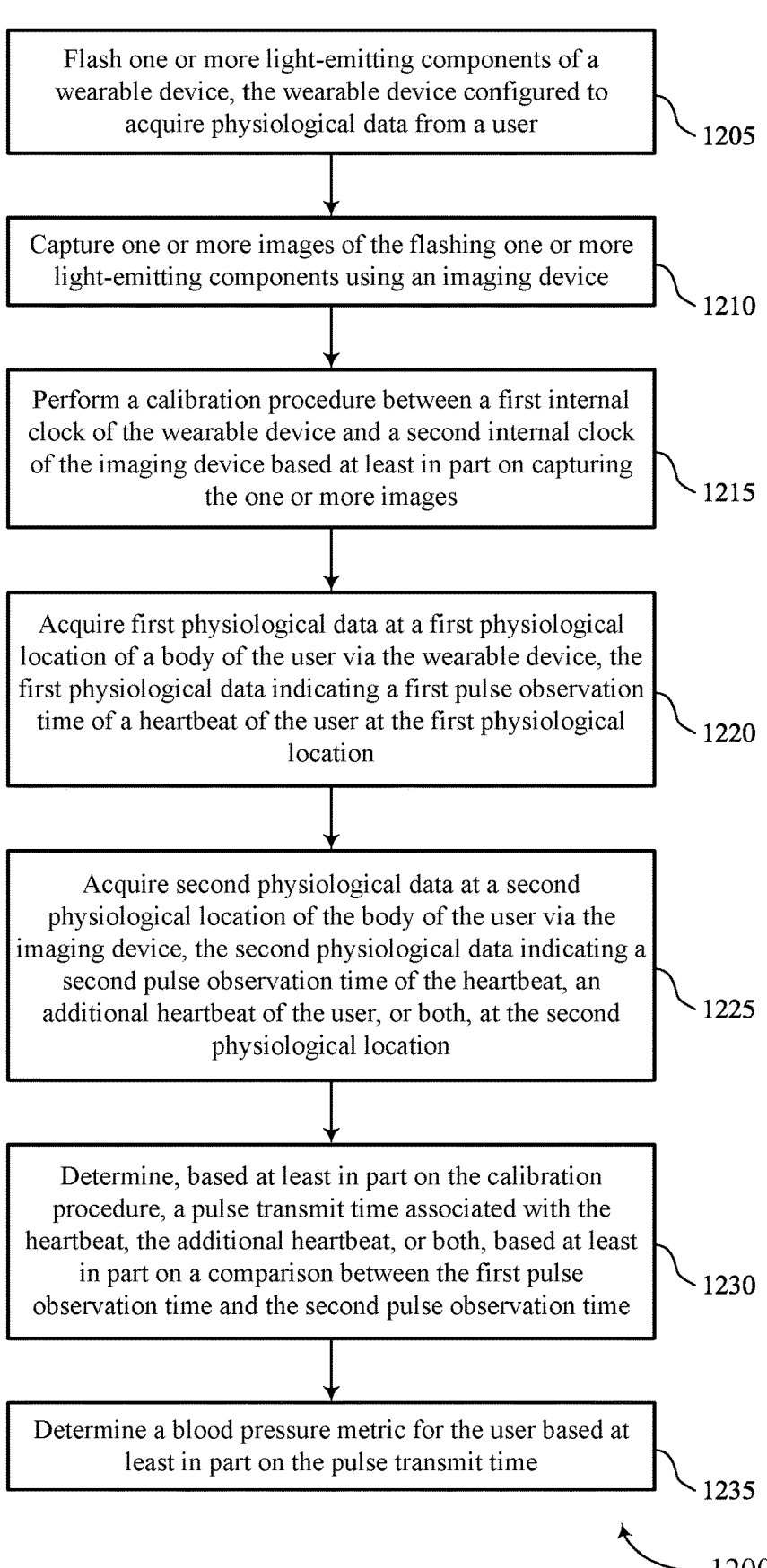
FIG. 12 shows a flowchart illustrating methods that support techniques for determining blood pressure based on a relative timing of pulses in accordance with aspects of the present disclosure.

FIG. 12 shows a flowchart illustrating a method 1200 that supports techniques for determining blood pressure based on a relative timing of pulses in accordance with aspects of the present disclosure. The operations of the method 1200 may be implemented by a user device or its components as described herein. For example, the operations of the method 1200 may be performed by a user device as described with reference to FIGS. 1 through 11. In some examples, a user device may execute a set of instructions to control the functional elements of the user device to perform the described functions. Additionally, or alternatively, the user device may perform aspects of the described functions using special-purpose hardware.

At 1205, the method may include flashing one or more light-emitting components of a wearable device, the wearable device configured to acquire physiological data from a user. The operations of block 1205 may be performed in accordance with examples as disclosed herein. In some examples, aspects of the operations of 1205 may be performed by a LED component 1025 as described with reference to FIG. 10.

At 1210, the method may include capturing one or more images of the flashing one or more light-emitting components using an imaging device. The operations of block 1210 may be performed in accordance with examples as disclosed herein. In some examples, aspects of the operations of 1210 may be performed by an imaging device component 1030 as described with reference to FIG. 10.

At 1215, the method may include performing a synchronization procedure to identify a delay between a first internal clock of the wearable device and a second internal clock of the imaging device based at least in part on capturing the one or more images. The operations of block 1215 may be performed in accordance with examples as disclosed herein. In some examples, aspects of the operations of 1215 may be performed by a synchronization procedure component 1035 as described with reference to FIG. 10.

At 1220, the method may include acquiring first physiological data at a first physiological location of a body of the user via the wearable device, the first physiological data indicating a first pulse observation time of a heartbeat of the user at the first physiological location. The operations of block 1220 may be performed in accordance with examples as disclosed herein. In some examples, aspects of the operations of 1220 may be performed by a data acquisition component 1040 as described with reference to FIG. 10.

At 1225, the method may include acquiring second physiological data at a second physiological location of the body of the user via the imaging device, the second physiological data indicating a second pulse observation time of the heartbeat, an additional heartbeat of the user, or both, at the second physiological location. The operations of block 1225 may be performed in accordance with examples as disclosed herein. In some examples, aspects of the operations of 1225 may be performed by a data acquisition component 1040 as described with reference to FIG. 10.

At 1230, the method may include determining a PTT associated with the heartbeat, the additional heartbeat, or both, based at least in part on the delay and a comparison between the first pulse observation time and the second pulse observation time. The operations of block 1230 may be performed in accordance with examples as disclosed herein. In some examples, aspects of the operations of 1230 may be performed by a PTT component 1045 as described with reference to FIG. 10.

At 1235, the method may include determining a blood pressure metric for the user based at least in part on the PTT. The operations of block 1235 may be performed in accordance with examples as disclosed herein. In some examples, aspects of the operations of 1235 may be performed by a blood pressure component 1050 as described with reference to FIG. 10.

It should be noted that the methods described above describe possible implementations, and that the operations and the steps may be rearranged or otherwise modified and that other implementations are possible. Furthermore, aspects from two or more of the methods may be combined.

A method by an apparatus is described. The method may include flashing one or more light-emitting components of a wearable device, the wearable device configured to acquire physiological data from a user, capturing one or more images of the flashing one or more light-emitting components using an imaging device, performing a synchronization procedure between a first internal clock of the wearable device and a second internal clock of the imaging device based at least in part on capturing the one or more images, acquiring first physiological data at a first physiological location of a body of the user via the wearable device, the first physiological data indicating a first pulse observation time of a heartbeat of the user at the first physiological location, acquiring second physiological data at a second physiological location of the body of the user via the imaging device, the second physiological data indicating a second pulse observation time of the heartbeat, an additional heartbeat of the user, or both, at the second physiological location, determining, based at least in part on the synchronization procedure, a PTT associated with the heartbeat, the additional heartbeat, or both, based at least in part on a comparison between the first pulse observation time and the second pulse observation time, and determining a blood pressure metric for the user based at least in part on the PTT.

An apparatus is described. The apparatus may include one or more memories storing processor executable code, and one or more processors coupled with the one or more memories. The one or more processors may individually or collectively operable to execute the code to cause the apparatus to flash one or more light-emitting components of a wearable device, the wearable device configured to acquire physiological data from a user, capture one or more images of the flashing one or more light-emitting components using an imaging device, perform a synchronization procedure between a first internal clock of the wearable device and a second internal clock of the imaging device based at least in part on capturing the one or more images, acquire first physiological data at a first physiological location of a body of the user via the wearable device, the first physiological data indicating a first pulse observation time of a heartbeat of the user at the first physiological location, acquire second physiological data at a second physiological location of the body of the user via the imaging device, the second physiological data indicating a second pulse observation time of the heartbeat, an additional heartbeat of the user, or both, at the second physiological location, determine, based at least in part on the synchronization procedure, a PTT associated with the heartbeat, the additional heartbeat, or both, based at least in part on a comparison between the first pulse observation time and the second pulse observation time, and determine a blood pressure metric for the user based at least in part on the PTT.

Another apparatus is described. The apparatus may include means for flashing one or more light-emitting components of a wearable device, the wearable device configured to acquire physiological data from a user, means for capturing one or more images of the flashing one or more light-emitting components using an imaging device, means for performing a synchronization procedure between a first internal clock of the wearable device and a second internal clock of the imaging device based at least in part on capturing the one or more images, means for acquiring first physiological data at a first physiological location of a body of the user via the wearable device, the first physiological data indicating a first pulse observation time of a heartbeat of the user at the first physiological location, means for acquiring second physiological data at a second physiological location of the body of the user via the imaging device, the second physiological data indicating a second pulse observation time of the heartbeat, an additional heartbeat of the user, or both, at the second physiological location, means for determining, based at least in part on the synchronization procedure, a PTT associated with the heartbeat, the additional heartbeat, or both, based at least in part on a comparison between the first pulse observation time and the second pulse observation time, and means for determining a blood pressure metric for the user based at least in part on the PTT.

A non-transitory computer-readable medium storing code is described. The code may include instructions executable by a processor to flash one or more light-emitting components of a wearable device, the wearable device configured to acquire physiological data from a user, capture one or more images of the flashing one or more light-emitting components using an imaging device, perform a synchronization procedure between a first internal clock of the wearable device and a second internal clock of the imaging device based at least in part on capturing the one or more images, acquire first physiological data at a first physiological location of a body of the user via the wearable device, the first physiological data indicating a first pulse observation time of a heartbeat of the user at the first physiological location, acquire second physiological data at a second physiological location of the body of the user via the imaging device, the second physiological data indicating a second pulse observation time of the heartbeat, an additional heartbeat of the user, or both, at the second physiological location, determine, based at least in part on the synchronization procedure, a PTT associated with the heartbeat, the additional heartbeat, or both, based at least in part on a comparison between the first pulse observation time and the second pulse observation time, and determine a blood pressure metric for the user based at least in part on the PTT.

In some examples of the method, apparatus, and non-transitory computer-readable medium described herein, performing the synchronization procedure may include operations, features, means, or instructions for determining a delay between when the one or more light-emitting components of the wearable device were flashed and when the flashing of the one or more light-emitting components was observed by the imaging device based at least in part on capturing the one or more images and selectively adjusting the PTT based at least in part on the delay, wherein determining the blood pressure metric may be based at least in part on selectively adjusting the PTT.

In some examples of the method, apparatus, and non-transitory computer-readable medium described herein, determining the delay may include operations, features, means, or instructions for receiving, from the wearable device, at least a first timestamp indicating a first time that the one or more light-emitting components were flashed and determining a second timestamp indicating a second time that the flashing of the one or more light-emitting components was observed by the imaging device based at least in part on capturing the one or more images, wherein the delay may be based at least in part on the first timestamp and the second timestamp.

Some examples of the method, apparatus, and non-transitory computer-readable medium described herein may further include operations, features, means, or instructions for receiving, via a user device communicatively coupled with the wearable device, a user input that initiates a blood pressure spot check procedure, wherein flashing the one or more light-emitting components, capturing the one or more images, performing the synchronization procedure, acquiring the first physiological data, acquiring the second physiological data, or any combination thereof, may be based at least in part on receiving the user input.

Some examples of the method, apparatus, and non-transitory computer-readable medium described herein may further include operations, features, means, or instructions for displaying, via a GUI of the user device and in response to the user input, a set of instructions for performing the synchronization procedure, wherein the set of instructions indicate for the user to capture the one or more images of the flashing one or more light-emitting components.

In some examples of the method, apparatus, and non-transitory computer-readable medium described herein, the first physiological data may be acquired by the wearable device using the one or more light-emitting components at a first power level and flashing the one or more light-emitting components comprises flashing the one or more light-emitting components at a second power level that may be greater than the first power level.

Some examples of the method, apparatus, and non-transitory computer-readable medium described herein may further include operations, features, means, or instructions for synchronizing a first sampling rate associated with the one or more light-emitting components and a second sampling rate associated with the imaging device based at least in part on performing the synchronization procedure, wherein the first physiological data may be acquired by the wearable device in accordance with the first sampling rate based at least in part on the synchronizing, and wherein the second physiological data may be acquired by the imaging device in accordance with the second sampling rate based at least in part on the synchronizing.

Some examples of the method, apparatus, and non-transitory computer-readable medium described herein may further include operations, features, means, or instructions for flashing, during a second time interval subsequent to the first time interval, the one or more light-emitting components of the wearable device, capturing one or more additional images of the flashing one or more light-emitting components using the imaging device during the second time interval, and performing a second synchronization procedure between the first internal clock of the wearable device and the second internal clock of the imaging device based at least in part on capturing the one or more additional images, wherein determining the PTT may be based at least in part on the synchronization procedure and the second synchronization procedure.

In some examples of the method, apparatus, and non-transitory computer-readable medium described herein, and the method, apparatuses, and non-transitory computer-readable medium may include further operations, features, means, or instructions for determining a plurality of PTTs associated with the user throughout the first time interval, selectively adjusting a first subset of the plurality of PTTs based at least in part on the first delay, and selectively adjusting a second subset of the plurality of PTTs based at least in part on the second delay, wherein determining the PTT may be based at least in part on selectively adjusting the first subset and the second subset of the plurality of PTTs based at least in part on the first delay and the second delay, respectively.

Some examples of the method, apparatus, and non-transitory computer-readable medium described herein may further include operations, features, means, or instructions for receiving one or more blood pressure metrics associated with a user that may be measured from an external device throughout a time interval, determining one or more PTTs associated with the user based at least in part on third physiological data acquired by the wearable device at the first physiological location throughout the time interval, and fourth physiological data acquired by the imaging device at the second physiological location throughout the time interval, and training a machine learning model to determine blood pressure metrics for the user based on PTTs observed between the first physiological location and the second physiological location based at least in part on inputting the one or more PTTs and the one or more blood pressure metrics into the machine learning model, wherein the blood pressure metric may be determined by the machine learning model based at least in part on training the machine learning model.

Some examples of the method, apparatus, and non-transitory computer-readable medium described herein may further include operations, features, means, or instructions for receiving an indication of a distance between the first physiological location and the second physiological location, wherein determining the blood pressure metric may be based at least in part on the PTT and the distance.

Some examples of the method, apparatus, and non-transitory computer-readable medium described herein may further include operations, features, means, or instructions for receiving, from the imaging device, one or more additional images of the body of the user between the first physiological location and the second physiological location and determining the distance between the first physiological location and the second physiological location based at least in part on the one or more additional images.

In some examples of the method, apparatus, and non-transitory computer-readable medium described herein, the first physiological location comprises a first location at a base of a finger of the user and the second physiological location comprises a second location at a tip of the finger of the user.

In some examples of the method, apparatus, and non-transitory computer-readable medium described herein, the imaging device comprises a second wearable device configured to acquire physiological data from the user.

In some examples of the method, apparatus, and non-transitory computer-readable medium described herein, the wearable device comprises a wearable ring device.

Another apparatus measuring blood pressure is described. The apparatus may include a wearable device comprising one or more light-emitting components, the wearable device configured to acquire physiological data from a user, an imaging device, one or more processors communicatively coupled with the wearable device and the imaging device, the one or more processors configured to, flash the one or more light-emitting components of the wearable device, capture one or more images of the flashing one or more light-emitting components using the imaging device, perform a synchronization procedure between a first internal clock of the wearable device and a second internal clock of the imaging device based at least in part on capturing the one or more images, acquire first physiological data at a first physiological location of a body of the user via the wearable device, the first physiological data indicating a first pulse observation time of a heartbeat of the user at the first physiological location, acquire second physiological data at a second physiological location of the body of the user via the imaging device, the second physiological data indicating a second pulse observation time of the heartbeat, an additional heartbeat of the user, or both, at the second physiological location, determine, based at least in part on the synchronization procedure, a PTT associated with the heartbeat, the additional heartbeat, or both, based at least in part on a comparison between the first pulse observation time and the second pulse observation time, and determine a blood pressure metric for the user based at least in part on the PTT.

In some examples of the apparatus, to perform the synchronization procedure, the one or more processors may be configured to determine a delay between when the one or more light-emitting components of the wearable device were flashed and when the flashing of the one or more light-emitting components was observed by the imaging device based at least in part on capturing the one or more images and selectively adjust the PTT based at least in part on the delay, wherein determining the blood pressure metric may be based at least in part on selectively adjusting the PTT.

In some examples of the apparatus, to determine the delay, the one or more processors may be configured to receive, from the wearable device, at least a first timestamp indicating a first time that the one or more light-emitting components were flashed and determine a second timestamp indicating a second time that the flashing of the one or more light-emitting components was observed by the imaging device based at least in part on capturing the one or more images, wherein the delay may be based at least in part on the first timestamp and the second timestamp.

In some examples of the apparatus, the one or more processors may be further configured to receive, via a user device communicatively coupled with the wearable device, a user input that initiates a blood pressure spot check procedure, wherein flashing the one or more light-emitting components, capturing the one or more images, performing the synchronization procedure, acquiring the first physiological data, acquiring the second physiological data, or any combination thereof, may be based at least in part on receiving the user input.

In some examples of the apparatus, the one or more processors may be positioned within the wearable device, the imaging device, one or more servers, or any combination thereof.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for estimating blood pressure comprising:

flashing one or more light-emitting components of a wearable device, the wearable device configured to acquire physiological data from a user;

capturing one or more images of the flashing one or more light-emitting components using an imaging device;

performing a synchronization procedure to identify a delay between a first internal clock of the wearable device and a second internal clock of the imaging device based at least in part on capturing the one or more images;

acquiring first physiological data at a first physiological location of a body of the user via the wearable device, the first physiological data indicating a first pulse observation time of a heartbeat of the user at the first physiological location;

acquiring second physiological data at a second physiological location of the body of the user via the imaging device, the second physiological data indicating a second pulse observation time of the heartbeat, an additional heartbeat of the user, or both, at the second physiological location;

selectively adjusting the first pulse observation time or the second pulse observation time based at least in part on the delay;

determining a pulse transmit time associated with the heartbeat, the additional heartbeat, or both, based at least in part on the delay and a comparison between the first pulse observation time and the second pulse observation time; and determining a blood pressure metric for the user based at least in part on the pulse transmit time, wherein determining the blood pressure metric is based at least in part on selectively adjusting the first pulse observation time or the second pulse observation time.

2. The method of claim 1, wherein performing the synchronization procedure comprises:

determining the delay between when the one or more light-emitting components of the wearable device were flashed and when the flashing of the one or more light-emitting components was observed by the imaging device based at least in part on capturing the one or more images.

3. The method of claim 2, wherein determining the delay comprises:

receiving, from the wearable device, at least a first timestamp indicating a first time that the one or more light-emitting components were flashed; and determining a second timestamp indicating a second time that the flashing of the one or more light-emitting components was observed by the imaging device based at least in part on capturing the one or more images, wherein the delay is based at least in part on the first timestamp and the second timestamp.

4. The method of claim 1, further comprising:

receiving, via a user device communicatively coupled with the wearable device, a user input that initiates a blood pressure spot check procedure, wherein flashing the one or more light-emitting components, capturing the one or more images, performing the synchronization procedure, acquiring the first physiological data, acquiring the second physiological data, or any combination thereof, is based at least in part on receiving the user input.

5. The method of claim 4, further comprising:

displaying, via a graphical user interface (GUI) of the user device and in response to the user input, a set of instructions for performing the synchronization procedure, wherein the set of instructions indicate for the user to capture the one or more images of the flashing one or more light-emitting components.

6. The method of claim 1, wherein the first physiological data is acquired by the wearable device using the one or more light-emitting components at a first power level, and wherein flashing the one or more light-emitting components comprises flashing the one or more light-emitting components at a second power level that is greater than the first power level.

7. The method of claim 1, further comprising:

synchronizing a first sampling rate associated with the one or more light-emitting components and a second sampling rate associated with the imaging device based at least in part on performing the synchronization procedure, wherein the first physiological data is acquired by the wearable device in accordance with the first sampling rate based at least in part on the synchronizing, and wherein the second physiological data is acquired by the imaging device in accordance with the second sampling rate based at least in part on the synchronizing.

8. The method of claim 1, wherein the first physiological data and the second physiological data are acquired throughout a first time interval, the method further comprising:

flashing, during a second time interval subsequent to the first time interval, the one or more light-emitting components of the wearable device;

capturing one or more additional images of the flashing one or more light-emitting components using the imaging device during the second time interval; and performing a second synchronization procedure to identify a second delay between the first internal clock of the wearable device and the second internal clock of the imaging device based at least in part on capturing the one or more additional images, wherein determining the pulse transmit time is based at least in part on the synchronization procedure and the second synchronization procedure.

9. The method of claim 8, wherein performing the synchronization procedure comprises determining a first delay between the first internal clock of the wearable device and the second internal clock of the imaging device, and wherein performing the second synchronization procedure comprises determining a second delay between the first internal clock of the wearable device and the second internal clock of the imaging device, the method further comprising:

determining a plurality of pulse observation times associated with the user throughout the first time interval;

selectively adjusting a first subset of the plurality of pulse observation times based at least in part on the first delay; and selectively adjusting a second subset of the plurality of pulse observation times based at least in part on the second delay, wherein determining the pulse transmit time is based at least in part on selectively adjusting the first subset and the second subset of the plurality of pulse observation times based at least in part on the first delay and the second delay, respectively.

10. The method of claim 1, further comprising:

receiving one or more blood pressure metrics associated with a user that are measured from an external device throughout a time interval;

determining one or more pulse transmit times associated with the user based at least in part on third physiological data acquired by the wearable device at the first physiological location throughout the time interval, and fourth physiological data acquired by the imaging device at the second physiological location throughout the time interval; and training a machine learning model to determine blood pressure metrics for the user based on pulse transmit times observed between the first physiological location and the second physiological location based at least in part on inputting the one or more pulse transmit times and the one or more blood pressure metrics into the machine learning model, wherein the blood pressure metric is determined by the machine learning model based at least in part on training the machine learning model.

11. The method of claim 1, further comprising:

receiving an indication of a distance between the first physiological location and the second physiological location, wherein determining the blood pressure metric is based at least in part on the pulse transmit time and the distance.

12. The method of claim 1, wherein the first physiological location comprises a first location at a base of a finger of the user, and wherein the second physiological location comprises a second location at a tip of the finger of the user.

13. The method of claim 1, wherein the imaging device comprises a second wearable device configured to acquire physiological data from the user.

14. The method of claim 1, wherein the wearable device comprises a wearable ring device.

15. A system for measuring blood pressure comprising:

a wearable device comprising one or more light-emitting components, the wearable device configured to acquire physiological data from a user;

an imaging device; and one or more processors communicatively coupled with the wearable device and the imaging device, the one or more processors configured to:

flash the one or more light-emitting components of the wearable device;

capture one or more images of the flashing one or more light-emitting components using the imaging device;

perform a synchronization procedure to identify a delay between a first internal clock of the wearable device and a second internal clock of the imaging device based at least in part on capturing the one or more images;

acquire first physiological data at a first physiological location of a body of the user via the wearable device, the first physiological data indicating a first pulse observation time of a heartbeat of the user at the first physiological location;

acquire second physiological data at a second physiological location of the body of the user via the imaging device, the second physiological data indicating a second pulse observation time of the heartbeat, an additional heartbeat of the user, or both, at the second physiological location;

selectively adjust the first pulse observation time or the second pulse observation time based at least in part on the delay;

determine a pulse transmit time associated with the heartbeat, the additional heartbeat, or both, based at least in part on the delay and a comparison between the first pulse observation time and the second pulse observation time; and determine a blood pressure metric for the user based at least in part on the pulse transmit time, wherein determining the blood pressure metric is based at least in part on selectively adjusting the first pulse observation time or the second pulse observation time.

16. The system of claim 15, wherein, to perform the synchronization procedure, the one or more processors are configured to:

determine the delay between when the one or more light-emitting components of the wearable device were flashed and when the flashing of the one or more light-emitting components was observed by the imaging device based at least in part on capturing the one or more images.

17. The system of claim 16, wherein, to determine the delay, the one or more processors are configured to:

receive, from the wearable device, at least a first timestamp indicating a first time that the one or more light-emitting components were flashed; and determine a second timestamp indicating a second time that the flashing of the one or more light-emitting components was observed by the imaging device based at least in part on capturing the one or more images, wherein the delay is based at least in part on the first timestamp and the second timestamp.

18. The system of claim 15, wherein the one or more processors are further configured to:

receive, via a user device communicatively coupled with the wearable device, a user input that initiates a blood pressure spot check procedure, wherein flashing the one or more light-emitting components, capturing the one or more images, performing the synchronization procedure, acquiring the first physiological data, acquiring the second physiological data, or any combination thereof, is based at least in part on receiving the user input.

19. The system of claim 18, wherein the one or more processors are further configured to:

display, via a graphical user interface (GUI) of the user device and in response to the user input, a set of instructions for performing the synchronization procedure, wherein the set of instructions indicate for the user to capture the one or more images of the flashing one or more light-emitting components.

* * * * *